United States Patent
Yang et al.

(10) Patent No.: US 10,449,216 B2
(45) Date of Patent: Oct. 22, 2019

(54) MODULATING DRUG EFFECTS AGAINST METABOTROPIC GLUTAMATE RECEPTOR WITH EXTRACELLULAR CALCIUM

(71) Applicant: GEORGIA STATE UNIVERSITY RESEARCH FOUNDATION, INC., Atlanta, GA (US)

(72) Inventors: Jenny J. Yang, Atlanta, GA (US); Jason Y. Jiang, West Roxbury, MA (US)

(73) Assignee: Georgia State University Research Foundation, Inc., Atlanta, GA (US)

(*) Notice: Subject to any disclaimer, the term of this patent is extended or adjusted under 35 U.S.C. 154(b) by 100 days.

(21) Appl. No.: 15/021,391

(22) PCT Filed: Sep. 15, 2014

(86) PCT No.: PCT/US2014/055577
§ 371 (c)(1),
(2) Date: Mar. 11, 2016

(87) PCT Pub. No.: WO2015/039003
PCT Pub. Date: Mar. 19, 2015

(65) Prior Publication Data
US 2016/0220603 A1    Aug. 4, 2016

Related U.S. Application Data

(60) Provisional application No. 61/877,579, filed on Sep. 13, 2013, provisional application No. 61/909,134, filed on Nov. 26, 2013.

(51) Int. Cl.
*A61K 33/06*    (2006.01)
*A61K 45/06*    (2006.01)
(Continued)

(52) U.S. Cl.
CPC ............ *A61K 33/06* (2013.01); *A61K 31/195* (2013.01); *A61K 31/198* (2013.01);
(Continued)

(58) Field of Classification Search
CPC .... A61K 33/06; A61K 31/195; A61K 31/198; A61K 31/352; A61K 31/4245; A61K 45/06; A61K 2300/00
See application file for complete search history.

(56) References Cited

U.S. PATENT DOCUMENTS

| | | | |
|---|---|---|---|
| 6,890,931 B2* | 5/2005 | Bear | A61K 31/00 514/277 |
| 2009/0239919 A1* | 9/2009 | Wood | C07C 235/64 514/371 |
| 2013/0209545 A1* | 8/2013 | Twidwell | A61K 31/4422 424/450 |

FOREIGN PATENT DOCUMENTS

| | | |
|---|---|---|
| CA | 2479109 | 8/2011 |
| EP | 2212284 | 4/2014 |

OTHER PUBLICATIONS

Lindsley et al., in Discovery of positive allosteric modulators for the metabotropic glutamate receptor subtype 5 from a series of N-(1,3-diphenyl-1H-pyrazol-5-yl)benzannides that potentiate receptor function in vivo, J. Med. Chem., 2004, vol. 47, 5825-5828 (Year: 2004).*

(Continued)

*Primary Examiner* — Kortney L. Klinkel
(74) *Attorney, Agent, or Firm* — Meunier Carlin & Curfman LLC

(57) ABSTRACT

Disclosed are methods for modulating the activity of an orthosteric or allosteric drug on a group I metabotropic glutamate receptor (mGluR) by increasing or decreasing the levels of extracellular $Ca^{2+}$.

5 Claims, 22 Drawing Sheets

Specification includes a Sequence Listing.

(51) Int. Cl.

| | | |
|---|---|---|
| | A61K 31/198 | (2006.01) |
| | A61K 31/352 | (2006.01) |
| | A61K 31/4245 | (2006.01) |
| | A61K 31/195 | (2006.01) |
| | A61N 1/36 | (2006.01) |

(52) U.S. Cl.
CPC ........ *A61K 31/352* (2013.01); *A61K 31/4245* (2013.01); *A61K 45/06* (2013.01); *A61N 1/36* (2013.01)

(56) References Cited

OTHER PUBLICATIONS

Mork et al., Therapeutic potential of metabotropic glutamate receptor modulators, Current Neuropharmacology, 2012, vol. 10, pp. 12-48 (Year: 2012).*
Wu et al., Neuroscience, 2004, vol. 123, pp. 507-514 (Year: 2004).*
Barnett, Receptor Theory, evaluating my therapeutic agent, 2010, slide 1-39 (Year: 2010).*
Pardridge (The Blood-Brain Barrier: Bottleneck in Brain Drug development, J. Am. Soc. Exper. NeuroTherapeutics, 2005, vol. 2, p. 3-14 (Year: 2005).*
Spooren et al., in Insight into the function of Group I and Group II metabotropic glutamate (mGlu) recetors: behaviouralcharacterization and implication for the treatment of CNS disorders, Behavioral Pharmacology, 2003, p. 257-277 (Year: 2003).*
Osikowicz et al., in The glutamatergic system as a target for neuropathic pain relief, Exp. Physio. 2013, vol. 98, p. 373-384 (Year: 2013).*
Montana et al., Metabotropic glutamate receptors as targets for analgesia: antagonism, activation, and allosteric modulation, Curr. Pharm. Biotechnol., 2011, vol. 12, p. 1681-1688 (Year: 2011).*
Lang, in Calcium causes brain cell loss in Parkinson's, New Scientist, 2010, pp. 1-2, https://www.newscientist.com/article/dn19711-calcium-causes-brain-cell-loss-in-parkinsons/ (Year: 2010).*
Acher, F. C., et al. (2011) Neuropharmacology 60:102-107.
Brauner-Osborne, H., et al. (1999) Neuroreport 10:3923-3925.
Chen, Y., et al. (2011) The Biochemical journal 435:711-722.
Conigrave, A. D., et al. (2007) The Journal of nutrition 137:1524S-1527S.
Cornell, W. D., et al. (1995) J. Am. Chem. Soc. 117:5179-5197.
Darden, T., et al. (1993) J. Chem. Phys. 98:10089-10092.
Dorr, P., et al. (2005) Antimicrobial agents and chemotherapy 49:4721-4732.
El Moustaine, D., et al. (2012) Proc Natl Acad Sci U S A. 109:16342-16347.
Geng, et al. (2016) eLife 5:e13662.
Goudet, C., et al. (2004) Proc Natl Acad Sci U S A. 101:378-383.
Haas, H. S., et al. (2007) The Oncol Rep 17:1399-1404.
Hemstapat, K., et al. (2006) Molecular pharmacology 70:616-626.
Hepler, R. W., et al. (2006) Biochemistry 45:15157-15167.
Huang, Y., et al. (2007) J Biol Chem 282:19000-19010.
Huang, Y., et al. (2009) Biochemistry 48:388-398.
Huang, Y., et al. (2010) J Biol Chem 285:35919-35931.
International Search Report and Written Opinion, issued in International Application No. PCT/US14/55577, dated Jan. 29, 2015.
Jiang, et al. (2014) J Biol Chem. 289: 1649-1661.
Jiang, Y., et al. (2010) J Biol Chem 285:33463-33474.
Jorgensen, W. L., et al. (1983) J. Chem. Phys. 79:926-935.
Kubo, Y., et al. (1998) Science 279:1722-1725.
Kunishima, N., et al. (2000) Nature 407:971-977.
Lavreysen, H., et al. (2003) Molecular pharmacology 63:1082-1093.
Levant, J. A., et al. (1973) The New England journal of medicine 289:555-558.
Lindsley, C. W., et al. (2004) Journal of medicinal chemistry 47:5825-5828.

Litschig, S., et al. (1999) Molecular pharmacology 55:453-461.
Nagar, B., et al. (1996) Nature 380:360-364.
Nash, M. S., et al. (2001) J Biol Chem 276:19286-19293.
Nemeth, E. F., et al. (1998) Proc Natl Acad Sci U S A. 95:4040-4045.
Ogawa, H., et al. (2010) Protein science: a publication of the Protein Society 19:544-557.
Rodriguez, A. L., et al. (2005) Molecular pharmacology 68:1793-1802.
Ryckaert, J. P., et al. (1977) J. Comput. Phys. 23:327-341.
Sato, T., et al. (2003) J Biol Chem 278:4314-4321.
Selkirk, J. V., et al. (2001) Neuropharmacology 40:645-656.
Smith, F. L., et al. (2004) Eur J Pharmacol 492:137-142.
Suzuki, Y., et al. (2004) J Biol Chem 279:35526-35534.
Tabata, T., et al. (2002) Mol Cell Neurosci 20:56-68.
Tateyama, M., et al. (2004) Nat Struct Mol Biol 11:637-642.
Tsuchiya, D., et al. (2002) Proc Natl Acad Sci U S A. 99:2660-2665.
Doshi, et al. (2009) J. Phys. Chem. 113:16590-16595.
Wang, L., et al. (2009) J Pharmacol Exp Ther 331:340-348.
Wang, X., et al. (2009) Proteins 75:787-798.
Wang, X., et al. (2010) Protein science: a publication of the Protein Society 19:1180-1190.
Whang, P. G., et al. (2008) Orthopedics 31(10).
Yuan, K., et al. (2011) J Biol Chem 286:24776-24784.
Zhang, et al. (2014) J Biol Chem 289: (48) 33529-33542.
Zhang, et al. (2014) J Biol Chem 289: (8): 5296-309.
Zhang, et al. (2014) PLOS One 9(11):e113622.
Zhang, et al. (2015) vol. 58: No. 1 pp. 14-27.
Zhang, F., et al. (2008) Proc Natl Acad Sci U S A. 105:20930-20934.
Zhang, F., et al. (2010) Proc Natl Acad Sci U S A. 107:4752-4757.
Zhang, Z., et al. (2002) J Biol Chem 277:33727-33735.
Amato, Russel J. et al., "Substituted 1-Phenyl-3-(pyridin-2-yl)urea Negative Allosteric Modulators of mGlu5: Discovery of a New Tool Compound VU0463841 with Activity in Rat Models of Cocaine Addiction," ACS Chemical Neuroscience, 2013, vol. 4; pp. 1217-1228.
Bespalov, Anton Y. et al., "Metabotropic Glutamate Receptor (mGluR5) Antagonist MPEP Attenuated Cue- and Schedule-Induced Reinstatement of Nicotine Self-Administration Behavior in Rats," Neuropharmacology, vol. 49, Supplement, 2005; pp. 167-178. (Abstract only).
Deng, Cheri X., "Targeted Drug Delivery Across the Blood-Brain Barrier Using Ultrasound Technique," Ther Deliv., Author Manuscript; Dec. 1, 2010; vol. 1, No. 6; pp. 819-848.
Dravolina, Olga A. et al., "mGlu1 Receptor Blockade Attenuates Cue- and Nicotine-Induced Reinstatement of Extinguished Nicotine Self-Administration Behavior in Rats," Neuropharmacology, vol. 52, Issue 2, Feb. 2007; pp. 263-269. (Abstract only).
Fefts, Andrew S. et al., "Discovery of VU0409106: A Negative Allosteric Modulator of mGlu5 With Activity in a Mouse Model of Anxiety," Bioorg Med Chem Lett., Nov. 1, 2013, 23(21); pp. 1-24.
Hempstapat, Kamondanai et al., "A Novel Class of Positive Allosteric Modulators of Metabotropic Glutamate Receptor Subtype 1 Interact with a Site Distinct from That of Negative Allosteric Modulators," Molecular Pharmacology, vol. 70, No. 2, 2006; pp. 616-626.
Lelyveld, Victor S. et al., "Challenges for Molecular Neuroimaging with MRI," Int J. Imaging Syst Technol. Mar. 2010 vol. 20, No. 1; pp. 71-79.
Lindsley, Craig. W. et al., "(3-Cyano-5-fluorophenyl)biaryl Negative Allosteric Modulators of mGlu5: Discovery of a New Tool Compound with Activity in the OSS Mouse Model of Addiction," ACS Chemical Neuroscience, 2011, vol. 2; pp. 471-482.
Olive, M.F. "Metabotropic Glutamate Receptor Ligands as Potential Therapeutics for Addiction," Curr Drug Abuse Rev. Jan. 2009; vol. 2, No. 1, 83-989; 29 pgs.
Tessari, Michela et al., "Antagonism at Metabotropic Glutamate 5 Receptors Inhibits Nicotine- and Cocaine-Taking Behaviours and Prevents Nicotine-Triggered Relapse to Nicotine-Seeking," European Journal of Pharmacology, vol. 499, Issues 1-2, Sep. 19, 2004; pp. 121-133. (Abstract only).

* cited by examiner

```
                         318 322 325
mGluR1        LIGSDGWADRDEVIE              328
mGluR5        LLGSDGWADRYDVTD              315
T1R3          WVASEAWLTS-DLVM              311
mGluR2        WVASDGWG-ALESVV              305
mGluR3        WVASDGWGAQ-ESII              311
mGluR7        WVGSDSWGSKINPLH              324
mGluR6        WVGSDSWGAKTSPIL              317
mGluR4        WMGSDSWGSKIAPVL              322
mGluR8        WIGSDSWGSKIAPVY              319
T1R2          WIASESWAIDPVLHN              312
T1R1          WVASEAWALSRHITG              311
CaSR          WLASEAWASSSLIAM              307
GABAbR1       VKLFEKWGWKKIATI              312
GABAbR2       QWIIPGWYEPSWWEQ              292
GABAbR3       LAPTSACPSAILLKA              331
```

FIG. 1A

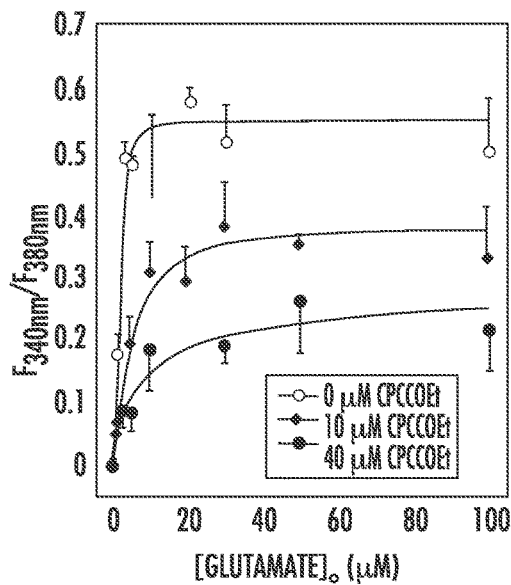 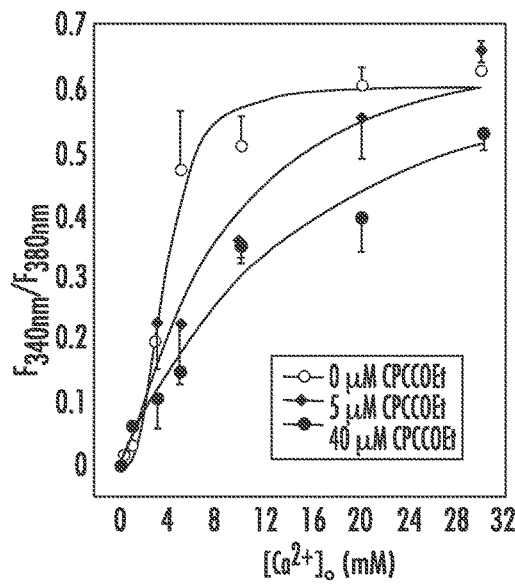
FIG. 5A  FIG. 5B
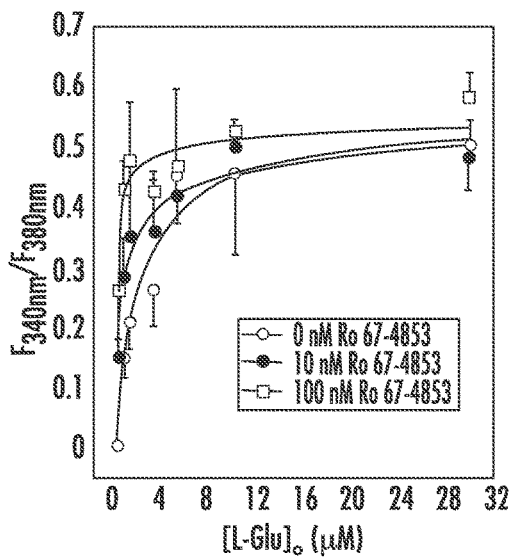 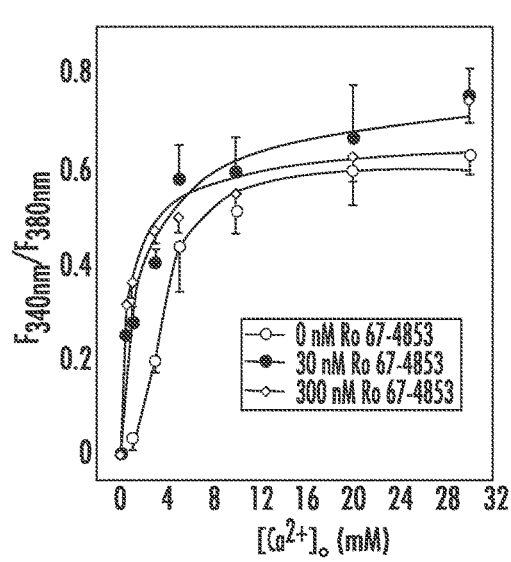
FIG. 6A  FIG. 6B

```
mGluR7   ------------------QEMYAPHSIRIEGDVTLGGLFPVH----AKGPSGVPCGDIKRENGIH  43
mGluR8   ------------------QEYA-HSIRVDGDIILGGLFPVH----AKGERGVPCGELKKEKGIH  41
mGluR4   --------------KPKGHPHMNSIRIDGDITLGGLFPVH----GRGSEGKACGELKKEKGIH  45
mGluR6   ------------------AGSV-RLAGGLTLGGLFPVH----ARGAAGRACGALKKEQGVH    38
mGluR2   ---------------EGPAKKVLTLEGDLVLGGLFPVH----QKGGPAEECGPVNEHRGIQ    42
mGluR3   -------------LGDHNFMRREIKIEGDVLGGLFPIN----EKGTGTEECGRINEDRGIQ    45
mGluR1   LPRMPDRKVLLAGASSQRSVARMDGDVII-GALFSVHHQPPAEKVPERKCGEIREQYGIQ    59
mGluR5   ---------------QSSERRVVAHMPGDIIIGALFSVHHQPTVDKVHERKCGAVREQYGIQ   47
                                        *                             * mGluR7   RLEAMLYALDQINSDPNLLPNVTLGARILDTCSRDYALEQSLTFVQALIQKDTSDV--R  101
mGluR8   RLEAMLYAIDQINKDPDLLSNITLGVRILDTCSRDYALEQSLTFVQALIEKDASDV--K   99
mGluR4   RLEAMLFALDRINNDPDLLPNITLGARILDTCSRDHALEQSLTFVQALIEKDGTEV--R  103
mGluR6   RLEAMLYALDRVNADPELLPGVRLGARLLDTCSRDYALEQALSFVQALIRGRGDGDEAS   98
mGluR2   RLEAMLFALDRINRDPHLLPGVRLGAHILDSCSKDTHALEQALDFVRASLSRGA-DGS-R 100
mGluR3   RLEAMLFAIDEINKDNYLLPGVKLGVHILDTCSRDTYALEQSLEFVRASLTKVDEAEY-M 104
mGluR1   RVEAMFHTLDKINADPVLLPNITLG-SEIRDSCWHSSV----ALEQSIEFIRDSLISIRDE 115
mGluR5   RVEAMLHTLERINSDPTLLPNITLG-CEIRDSCWHSAV----ALEQSIEFIRDSLIS-SEE 102
            * ***  * *                          * *         * mGluR7   CTN-GEPPVFVKPE--KVVGVIGASGSSVSIMVANILRLFQIPQISY----ASTAPELSDD  155
mGluR8   CAN-GDPPIPFTKPD--KISGVIGAAASSVSIMVANILRLFKIPQISY----ASTAPELSDN  153
mGluR4   CGS-GGPPIIITKPE--RVVGVIGASGSSVSIMVANILRLFKIPQISY----ASTAPDLSDN  157
mGluR6   VRCPGGVPPLRSAPPERVVAVVGASASSVSIMVANVLRLFAIPQISY----ASTAPELSDS  155
mGluR2   HICPDGSYATHSDAPTAVTGVIGGSYSDVSIQVANLLRLFQIPQISY----ASTSAKLSDK  157
mGluR3   CP--DGSYAIQENIPLLIAGVIGGSYSSVSIQVANLLRLFQIPQISY----ASTSAKLSDK  159
mGluR1   KDGLNRCLPDGQTLPPGRTKKPIAGVIGPGSSVAIQVQNLLQLFDIPQIAYSATSIDLS  175
mGluR5   EEGLVRCVDGSSSF----RSKKPIVGVIGPGSSSVAIQVQNLLQLFNIPQIAYSATSMDLS  159
      *                                                * mGluR7   RRY--DFFSRVVPPDSFQAQAMVDIVKALGWNYVSTLASEGSYGEKGVESFTQISKEAGG  213
mGluR8   TRY--DFFSRVVPPDSYQAQAMVDIVTALGWNYVSTLASEGNYGESGVEAFTQISREIGG  211
mGluR4   SRY--DFFSRVVPSDTYQAQAMVDIVRALKWNYVSTLASEGSYGESGVEAFIQKSRENGG  215
mGluR6   TRY--DFFSRVVPPDSYQAQAMVDIVRALGWNYVSTLASEGNYGESGVEAPVQISREAGG  213
mGluR2   SRY--DYFARTVPPDFFQAKAMAEILRFFNWTYVSTVASEGDYGETGIEAPELEAR-ARN  214
mGluR3   SRY--DYFARTVPPDFYQAKAMAEILRFFNWTYVSTVASEGDYGETGIEAFEQEAR-LRN  216
mGluR1   DKTLYKYFLRVVPSDTLQARAMLDIVKRYNWTYVSAVHTEGNYGESGMDAFKELAA-QEG  234
mGluR5   DKTLFKYFMRVVPSDAQQARAMVDIVKRYNWTYVSAVHTEGNYGESGMEAFKDMSA-KEG  218
           * ** *       *    * *     ***  *         * mGluR7   LCIAQSVRIPQERKDRTIDFDRIIKQLLDTP-NSRAVVIFANDEDIKQILAAAKRADQVG  272
mGluR8   VCIAQSQKIPREPRPGEFE--KIIKRLLETP-NARAVIMFANEDDIRRRILEAAKKLNQSG  268
mGluR4   VCIAQSVKIPREPKTGEFD--KIIKRLLETS-NARGIIIFANEDDIRRRVLEAARRANQTG  272
mGluR6   VCIAQSIKIPREPKPGEFH--KVIRRLMETP-NARGIIIFANEDDIRRRVLEATRQANLTG  270
mGluR2   ICVAT---SEKVGRAMSRAAFEGVVRALLQKP-SARVAVLFTRSEDARELLAATQRLNASF  271
mGluR3   ICIATAEKVGRSNIRKSYD--SVIRELLQKP-NARVVVLFMRSDDSRELIAAANRVNASF  273
mGluR1   LCIAHSDKIYSNAGEKSFD--RLLRKLRERLPKARVVVCFCEGMTVRGLLSAMRRLGVVG  292
mGluR5   ICIAHSYKIYSNAGEQSFD--KLLKKLRSHLPKARVVACFCEGMTVRGLLMAMRRLGLAG  276
           *   *                 *              *       *         * mGluR7   HFLWVGSDSWGSKINPLHQHEDIAEGAITIQPKRATVEGFDAYFTSRTLENNRRNVWFAE  332
mGluR8   HFLWIGSDSWGSKIAPVYQQEEIAEGAVTILPKRASIDGFDRYFRSRTLANNRRNVWFAE  328
mGluR4   HFFWMGSDSWGSKSAPVLRLEEVAEGAVTILPKRMSVRGFDRYFSSRTLDNNRRNIWFAE  332
mGluR6   HFLWVGSDSWGSKISPILNLEEEAVGAITILPKRASIDGFDQYFMTRSLENNRRNIWFAE  330
mGluR2   TWVASDGWGALESVV--AGSERAAEGAITIELASYPISDFASYFQSLDPWNNSRNPWFRE  329
mGluR3   TWVASDGWGAQESIV--KGSEHVAYGAITLELASHPVRQFDRYFQSLNPYNNHRNPWFRD  331
mGluR1   EFSLIGSDGWADRDEVIEGYEVEANGGITIKLQSPEVRSFDDYFLKLRLDTNTRNPWFPE  352
mGluR5   EFLLLGSDGWADRYDVTDGYQREAVGGITIKLQSPDVKWFDDYYLKLRPETNLRNPWFQE  336
                * *                                                 * mGluR7   YWEENFNCKLTISGSKKEDTDRKCTGQERIGKDSNYEQEGKVQFVIDAVYAMAHALHHMN  392
mGluR8   FWEENFGCKLGSHGKRN-SHIKKCTGLERIARDSSYEQEGKVQFVIDAVYSMAYALHNMH  387
mGluR4   FWEDNFHCKLSRHALKKGSHIKKCTNRERIGQDSSAYEQEGKVQFVIDAVYAMGHALHAMH  392
mGluR6   FWEENFNCKLTSSGGQSDDSTRKCTGEERIGQDSAYEQEGKVQFVIDAVYAIAHALHSMH  390
mGluR2   FWEERFHCSFRQRDCAA------HSLRA-------VPFEQESKIMFVVNAVYAMAHALHNMH  378
mGluR3   FWEQKFQCSLQNKRNHRQ----VCDKHLAID-SSNYEQESKIMFVVNAVYAMAHALHKMQ  386
mGluR1   FWQHRFQCRLPGHLLENPNFKKVCTGNESLEENYVQD--SKMGFVINAIYAMAHGLQNMH  410
mGluR5   FWQHRFQCRLEGFAQENSKYNKTCNSSLTLRTHHVQD--SKMGFVINAIYSMAYGLHNMQ  394
          * *    *                                 *** *      *        *  *
```

FIG. 22A

```
mGluR7   KDLCADYRGVCPEMEQAGGKKLLK----YIRHVNFNGSAGTPV--MFNKNGDAPGRYDIF 446
mGluR8   KERCPGYIGLCPRMVTIDGKELLG----YIRAVNFNGSAGTPV--TFNENGDAPGRYDIF 441
mGluR4   RDLCPGRVGLCPRMDPVDGTQLLK----YIRNVNFSGIAGNPV--TFNENGDAPGRYDIY 446
mGluR6   QALCPGHTGLCPAMEPTDGRTLLH----YIRAVRFNGSAGTPV--MFNENGDAPGRYDIF 444
mGluR2   RALCPNTTHLCDAMRPVNGRRLYKDFVLNVKFDAPFRPADTDDEVRFDRFGDGIGRYNIF 438
mGluR3   RTLCPNTTKLCDAMKILDGKKLYKEYLLKINFTAPFNPNKGAD--SIVKFDTFGDGMGRY 444
mGluR1   HALCPGHVGLCDAMKPIDGRKLLD----FLIKSSFVGVSGEEV--WFDEKGDAPGRYDIM 464
mGluR5   MSLCPGYAGLCDAMKPIDGRKLLD----SLMKTNFTGVSGDMI--LFDENGDSPGRYEIM 448
              *      *    *    *   * mGluR7   QYQ-TTNTTNPGYRLIGQWTDELQLNIEDM----QWGKGVREIPS--SVCTLPCKPGQRKK 500
mGluR8   QYQ-INNKSTE-YKIIGHWTNQLHLKVEDM----QWANREHTHPA--SVCSLPCKPGERKK 494
mGluR4   QYQ-LRNGSAE-YKVIGSWTDHLHLRIERM----QWPGSGQQLPR--SICSLPCQPGERKK 499
mGluR6   QYQ-ATNGSASSGGYQAVGQWAEALRLDME----VLRWSGDPHEVPPSQCSLPCGPGERKK 500
mGluR2   TYL-RAG---SGRYRYQKVGYWAEGLTLDTSFIPWASPSAGPLPA--SRCSEPCLQNEVKS 493
mGluR3   NVF-NLQQTGGKYSYLKVGHWA--ETLSLD----VDSIHWSRNSVPTSQCSDPCAPNEMKN 498
mGluR1   NLQYTEANRYDYVHVGTWHEGVLNIDDYKI---QMNKSGMV--R--SVCSEPCLKGQIKV 517
mGluR5   NF--KEMGKDYFDYINVGSWDNGELKMDDD----EVWSKKNNIIR--SVCSEPCEKGQIKV 501
                                                              *  *  ** mGluR7   TQKG-TPCCWTCEPCDGYQYQFDEMTCQHCPYDQRPNENRTGCQNIPIIKLEWHSPWAVI 559
mGluR8   TVKG-VPCCWHCERCEGYNYQVDELSCELCPLDQRPNINRTGCQRIPIIKLEWHSPWAVV 553
mGluR4   TVKG-MACCWHCEPCTGYQYQVDRYTCKTCPYDMRPTENRTSCQPIPIVKLEWDSPWAVL 558
mGluR6   MVKG-VPCCWHCEACDGYRPQVDEFTCEACPGDMRPTPNHTGCRPTPVVRLTWSSPWAAL 559
mGluR2   VQPG-EVCCWLCIPCQPYEYRLDEFTCADCGLGYWPNASLTGCFELPQEYIRWGDAWAVG 552
mGluR3   MQPG-DVCCWICIPCEPYEYLVDEFTCMDCGPGQWPTADLSGCYNLPEDYIKWEDAWAIG 557
mGluR1   IRKGEVSCCWICTACKENEFVQDEFTCRACDLGWWPNAELTGCEPIPVRYLEWSDIESII 577
mGluR5   IRKGEVSCCWTCTPCKENEYVFDEYTCKACQLGSWPTDDLTGCDLIPVQYLRWGDPEPIA 561
             *  ****  *        *      *       *      *   *      * mGluR7   PVFLAMLGIIATIFVMATFIRYNDTPIVRASGRELSYVLLTGIFLCYIITFLMIAKPDVA 619
mGluR8   PVFIAILGIIATTFVIVTFVRYNDTPIVRASGRELSYVLLTGIFLCYSITFLMIAAPDTI 613
mGluR4   PLFLAVVGIAATLFVVVTFVRYNDTPIVKASGRELSYVLLAGIFLCYATTFLMIAEPDLG 618
mGluR6   PLLLAVLGIMATTTIMATFMRHNDTPIVRASGRELSYVLLTGIFLIYAITFLMVAEPCAA 619
mGluR2   PVTIACLGALATLFVLGVFVRHNATPVVKASGRELCYILLGGVFLCYCMTFVFIAKPSTA 612
mGluR3   PVTIACLGFLCTCIVITVFIKHNNTPLVKASGRELCYILLFGVSLSYCMTFFFIAKPSPV 617
mGluR1   AIAFSCLGILVTLFVTLIFVLYRDTPVVKSSSRELCYIILAGIFLGYVCPFTLIAKPTTT 637
mGluR5   AVVFACLGLLATLFVTVIFIIYRDTPVVKSSSRELCYIILAGICLGYLCTFCLIAKPKQI 621
              *      *    *        *  * ** *  *        * * mGluR7   VCSFRRVFLGLGMCISYAALLTKTNRIYRIFEQGKKSVTAPRLISPTSQLAITSSLISVQ 679
mGluR8   ICSFRRRIFLGLGMCFSYAALLTKTNRIHRIFEQGKKSVTAPKFISPASQLVITFSLISVQ 673
mGluR4   TCSLRRIFLGLGMSISYAALLTKTNRIYRIFEQGKRSVSAPRFISPASQLAITFILISLQ 678
mGluR6   ICAARRLLLGLGTTLSYSALLTKTNRIYRIFEQGKRSVTPPPFISPTSQLVITFGLTSLQ 679
mGluR2   VCTLRRLGLGTAFSVCYSALLTKTNRIARIFGGAREGAQRPRFISPASQVAICLALIS-- 670
mGluR3   ICALRRLGLGTSFAICYSALLTKTNCIARIFDGVKNGAQRPKFISPSSQVFICLGLIL-- 675
mGluR1   SCYLQRLLVGLSSAMCYSALVTKTNRIARILAGSKKKICTRKP-RFMSAWAQV-IIASIL 695
mGluR5   YCYLQRIGIGLSPAMSYSALVTKTNRIARILAGSKKKICTKKP-RFMSACAQL-VIAFIL 679
          *     *       *   ** * ***   * mGluR7   LLGVFIWFGVDPPNIIIDYDEHKTMNPEQAR--GVLKCDITDLQIICSLGYSILLMVTCT 737
mGluR8   LLGVFVWFVVDPPHTIIDYGEQRTLDPENAR--GVLKCDISDLSLICSLGYSILLMVTCT 731
mGluR4   LLGICVWFVVDPSHSVVDFQDQRTLDPRFAR--GVLKCDISDLSLICLLGYSMLLMVTCT 736
mGluR6   VVGVIAWLGAQPPHSVIDYEEQRTVDPEQAR--GVLKCDMSDLSLIGCLGYSLLLMVTCT 737
mGluR2   --GQLLIVAAWLVVEAPGT----GKETAPERREVVTLRCNHRDASMLGSLAYNVLLIALCT 725
mGluR3   --VQIMVSVWLILETPGT----RRYTLPEKRETVILKCNVKDSSMLISLTYDVVLVILCT 730
mGluR1   ISVQLTLVVTLIIMEPPMP----ILSYPSIKE--VYLICNTSNLGVVAPVGYNGLLIMSCT 750
mGluR5   ICIQLGIIVALFIMEPPDI---MHDYPSIRE--VYLICNTTNLGVVTPLGYNGLLILSCT 734
                                         * *                 *   * mGluR7   VYAIKTRGVPENFNEAKPIGFTMYTTCIVWLAFIPIFFGTAQS------------------ 780
mGluR8   VYAIKTRGVPETFNEAKPIGFTMYTTCIIWLAFIPIFFGTAQS------------------ 774
mGluR4   VYAIKTRGVPETFNEAKPIGFTMYTTCIVWLAFIPIFFGTSQS------------------ 779
mGluR6   VYAIKARGVPETFNEAKPIGFTMYTTCIIWLAFVPIFFGTAQS------------------ 780
mGluR2   LYAFKTRKCPENFNEAKFIGFTMYTTCIIWLAFLPIFYVTS-S------------------ 767
mGluR3   VYAFKTRKCPENFNEAKFIGFTMYTTCIIWLAFLPIFYVTS-S------------------ 772
mGluR1   YYAFKTRNVPANFNEAKYIAFTMYTTCIIWLAFVPIYFGSNYKIITTCFAVSLSVTVALG 810
mGluR5   FYAFKTRNVPANFNEAKYIAFTMYTTCIIWLAFVPIYFGSNYKIITMCFSVSLSATVALG 794
         **  *  *  **** *********   ****   **
```

FIG. 22B

```
mGluR7  ------------------AEKLYIQTTTLTISMNLSASVALGMLYM--PKVYIIIFHPELNVQ  823
mGluR8  ------------------AEKMYIQTTTLTVSMSLSASVSLGMLYM--PKVYIIIFHPEQNVQ  817
mGluR4  ------------------ADKLYIQTTTLTVSVSLSASVSLGMLYM--PKVYIILFHPEQNVP  822
mGluR6  ------------------AEKIYIQTTTLTVSLSLSASVSLGMLYV--PKTYVILFHPEQNVQ  823
mGluR2  ------------------DYRVQ--TTTMCVSVSLSGSVVLGCLFA--PKLHIILFQPQKNVV  808
mGluR3  ------------------DYRVQ--TTTMCISVSLSGFVVLGCLFA--PKVHIVLFQPQKNVV  813
mGluR1  CMFTPKMYIIIAKPERNVRSA-FTTSDVVRMHVGDGKLPCRSNTFLNIFRRKKPGAGNAN    869
mGluR5  CMFVPKVYIILAKPERNVRSA-FTTSTVVRMHVGDGK--SSSA--ASRSSSLVNLWKRRG    849
                                        ** mGluR7  KRK----RSFKAV---------------VTAATMSSRLSHKPSDRPNGEAKTELCENVDPNSP  867
mGluR8  KRK----RSFKAV---------------VTAATMQSKLIQKGNDRPNGEVKSELCESLETNTS  861
mGluR4  KRK----RSLKAV---------------VTAATMSNKFTQKGNFRPNGEAKSELCENLE-TPA  865
mGluR6  KRK----RSLKKT---------------STMAAPPQNENAEDAK-------------------  848
mGluR2  SHR----APTSRF---------------GSAAPRASANLGQGSGSQFVPTVC-----------  841
mGluR3  THR----LHLNRF---------------SVSGTA--TTYSQSSASTYVPTVC-----------  844
mGluR1  SNG----KSVSWSEP-------------GGRQAPKGQHVWQRLSVHVKTNETACNQTAVIKPL  915
mGluR5  SSGETLRYKDRRLAQHKSEIECFTPKGSMGNGGRATMSSSNGKSVTWAQNEKSTRGQHLW    909 mGluR7  AAKKKYVSYN------NLVI------------------------------------  881
mGluR8  STKTTYISYS------NHSI------------------------------------  875
mGluR4  LATKQTYVTY------TNHAI-----------------------------------  880
mGluR6  --------------------------------------------------------
mGluR2  -NGREVVDST------TSSL------------------------------------  854
mGluR3  -NGREVLDST------TSSL------------------------------------  857
mGluR1  TKSYQGSGKSLTFS-DASTKTLYNVEEEDNTPSAHFSPPSSPSMVVHRRGPPVATTPPLP  974
mGluR5  QRLSVHINKKENPNQTAVIKPFPKSTENRGP-GAAAGGGSGPGVAGAGNA--GCTATGGP  966 mGluR7  --------------------------------------------------------
mGluR8  --------------------------------------------------------
mGluR4  --------------------------------------------------------
mGluR6  --------------------------------------------------------
mGluR2  --------------------------------------------------------
mGluR3  --------------------------------------------------------
mGluR1  PHLTAEETPLFLADSVIPKGLPPPLPQQQPQQPPPQQPPQQPKSLM------DQLQGVVTN  1029
mGluR5  EPPDAGPKALYDVAEAEESFPAAA------------------RPRSPSPISTLSHLAGSAGR  1010 mGluR7  --------------------------------------------------------
mGluR8  --------------------------------------------------------
mGluR4  --------------------------------------------------------
mGluR6  --------------------------------------------------------
mGluR2  --------------------------------------------------------
mGluR3  --------------------------------------------------------
mGluR1  FGSGIPDFHAVLAGPGTPGNSLRSLYPPPPPPQHLQMLPLHLSTFQEESISPPGEDIDDD  1089
mGluR5  TDDDAPSLHSETAARS--SSSQGSLME----QISSVVTRFTANISELNSMM----LSTAAT  1061 mGluR7  --------------------------------------------------------
mGluR8  --------------------------------------------------------
mGluR4  --------------------------------------------------------
mGluR6  --------------------------------------------------------
mGluR2  --------------------------------------------------------
mGluR3  --------------------------------------------------------
mGluR1  SERFKLLQEFVYEREG--------NTEEDELEEEEDLPTASKLTPEDSP--------   1130
mGluR5  PGPPGTPICSSYLIPKEIQLPTTMTTFAEIQPLPAIEVTGGAQGATGVSPAQETPTGAES  1121 mGluR7  --------------------------------------------------------
mGluR8  --------------------------------------------------------
mGluR4  --------------------------------------------------------
mGluR6  --------------------------------------------------------
mGluR2  --------------------------------------------------------
mGluR3  --------------------------------------------------------
mGluR1  -----------ALTPPSPFRDSVASGSSVPSSPVSESVLCTPPNVTYASVILRDYKQSSSTL  1181
mGluR5  APGKPDLEELVALTPPSPFRDSVDSGSTTPNSPVSESALCIPSSPKYDTLIIRDYTQSSSTL  1183
```

FIG. 22C

MODULATING DRUG EFFECTS AGAINST METABOTROPIC GLUTAMATE RECEPTOR WITH EXTRACELLULAR CALCIUM

CROSS-REFERENCE TO RELATED APPLICATIONS

This application claims benefit of U.S. Provisional Application No. 61/877,579, filed Sep. 13, 2013, and U.S. Provisional Application No. 61/909,134, filed Nov. 26, 2013, which are hereby incorporated herein by reference in its entirety.

BACKGROUND

The eight subtypes of metabotropic glutamate receptors (mGluRs) belong to family C G protein-coupled receptors (GPCRs) and possess a large extracellular domain (ECD), seven transmembrane domains (TMD) and cytosolic C-terminal tail. The mGluRs are widely expressed in the central nervous system and play critical roles in regulating neuronal excitability and synaptic plasticity at both excitatory and inhibitory synapses (Neyman, S., et al. (2008) The European journal of neuroscience 27:1345-1352). Extensive structural studies have revealed that the endogenous agonist, L-Glutamate (L-Glu), the major excitatory neurotransmitter in the central nervous system, binds at the hinge region of the ECD within the receptor's Venus Fly Trap (VFT) motif to activate the protein. This subsequently stimulates phospholipase C (PLC) and leads to accumulation of inositol trisphosphate (IP$_3$) and an increase of intracellular calcium concentration ([Ca$^{2+}$]$_i$) (Lavreysen, H., et al. (2003) Molecular pharmacology 63:1082-1093; Lindsley, C. W., et al. (2004) Journal of medicinal chemistry 47:5825-5828; Kubo, Y., et al. (1998) Science 279:1722-1725).

In recent years, mGluRs have received increasing interest as potential drug targets for the treatment of a range of psychiatric and neurological diseases (Whang, P. G., et al. (2008) Orthopedics 31(10)) (FIG. 1). The ligands targeting mGluRs can be classified as orthosteric agonists and antagonists as well as allosteric modulators. Orthosteric agonists and antagonists induce and attenuate, respectively, the activity of the receptor by competitively binding to the L-Glu binding pocket. L-Quisqualate (L-Quis), the most potent agonist of mGluR1 reported to date (Yuan, K., et al. (2011) J Biol Chem 286:24776-24784; Chen, Y., et al. (2011) The Biochemical journal 435:711-722), has been speculated to share nearly the same binding pocket as L-Glu (Levant, J. A., et al. (1973) The New England journal of medicine 289:555-558; Sato, T., et al. (2003) J Biol Chem 278:4314-4321). In contrast, (S)-α-Methyl-4-carboxyphenylglycine ("(s)-MCPG") is an analog of L-Glu and a non-selective competitive antagonist that has been shown to occupy the L-Glu binding pocket, thereby blocking the function of group I/II members in the mGluR family (Tsuchiya, D., et al. (2002) Proc Natl Acad Sci USA. 99:2660-2665). On the other hand, allosteric modulators bind to sites other than the orthosteric center to affect the activity of the receptor. The molecule (9H-xanthene-9-carbonyl) carbamic acid butyl ester ("Ro 67-4853") is a positive allosteric modulator (PAM) of mGluR1 that enhances the potency of L-Glu by interacting with the TMDs of the receptor. The molecule (−)-ethyl (7E)-7-hydroxyimino-1,7a-dihydrocyclopropa[b] chromene-1a-carboxylate ("CPCCOEt") is a negative allosteric modulator (NAM) that inhibits the activation of mGluR1 by L-Glu by specifically binding to a site residing at the third extracellular loop of mGluR1α (Nagar, B., et al. (1996) Nature 380:360-364).

SUMMARY

Disclosed are methods for modulating the activity of an orthosteric or allosteric drug on a group I metabotropic glutamate receptor (mGluR), such as mGluR1, mGluR5, or a combination thereof, by increasing or decreasing extracellular Ca$^{2+}$. The orthosteric or allosteric drugs can be an agonists, antagonists, or allosteric regulators. Also disclosed is a method for treating a disease or disorder in a subject that is fully or partially mediated by a group I mGluRs.

Selective pharmacological antagonists and/or negative allosteric modulators of group I mGluRs are potential therapeutic agents for the treatment of numerous disorders of the central nervous system (CNS), including depression, anxiety, drug addiction, chronic pain, Fragile X syndrome (FXS), autism spectrum disorders (ASD), Parkinson's disease, and gastroesophageal reflux disease. Moreover, agonists and positive allosteric modulators (PAMs) of group I mGluRs are potential therapeutic agents for the treatment of other CNS disorders, including schizophrenia, cognitive deficits associated with chronic drug use, and deficits in extinction learning. Therefore, these activities can be enhanced by increasing extracellular Ca$^{2+}$.

The method can involve administering to the subject an orthosteric agonist, orthosteric antagonist, or allosteric modulator of one or more group I mGluRs (such as those set forth in Table 1A or 1B). The method can further involve administering to the subject a calcium agent for increasing or decreasing extracellular Ca$^{2+}$ levels in an amount to modulate the activity of the orthosteric agonist, orthosteric antagonist, or allosteric modulator. Therefore, in some embodiments, the orthosteric agonist, orthosteric antagonist, or allosteric modulator may be administered at a dosage below its normally effective dosage (ED) if administered with the calcium agent. For example, the orthosteric agonist, orthosteric antagonist, or allosteric modulator may be administered in an amount that is at least 10, 20, 30, 40, 50, 60, 70, 80, or 90% below its normal ED$_{50}$.

In some aspects of the disclosed method, the orthosteric agonist, orthosteric antagonist, or allosteric modulator is formulated with the calcium agent in a single dosage unit. Therefore, also disclosed is a composition comprising an orthosteric agonist, orthosteric antagonist, or allosteric modulator of one or more mGluRs (referred to collectively herein as "mGluR orthosteric or allosteric drug"), in combination with a calcium agent. This composition can contain the mGluR orthosteric or allosteric drug and the calcium agent in amounts and ratios sufficient to provide an effective dose to promote or inhibit mGluR activity. It is understood that the amount of calcium agent in the composition can affect the amount of mGluR orthosteric or allosteric drug needed for an effective dose. Optimal amounts and ratios can therefore be determined empirically for each combination and intended use.

In some embodiments, the calcium agent is a food or calcium supplement. In some embodiments, the calcium agent is a neurotransmitter or amino acid that affects sensitivity of the mGluR to calcium. In some embodiments, the calcium agent is a neurotransmitter that promotes calcium release from cellular calcium stores. In some embodiments, the calcium agent is an electric or mechanical stimulation.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B are schematic views of the binding sites for $[Ca^{2+}]_o$, L-Glu, L-Quis and (s)-MCPG in the mGluR1α ECD. FIG. 1A shows the $[Ca^{2+}]_o$-binding site is highly conserved in group I mGluRs and T1R3. In contrast, while sequence alignment suggests that the $[Ca^{2+}]_o$ binding site is highly conserved in group I mGluRs, it is not conserved in other members of the subfamily. FIG. 1B shows L-Glu, L-Quis and (s)-MCPG binding pockets (diamond), and scheme of binding sites for various classes of ligands acting on mGluR1α. Similar to the L-Glu binding pocket, Y74, R78, S165, T188, Y236, D318, and K409 form the L-Quis binding pocket. Similar residues, Y74, W110, S165, T188, Y236, D318 and K409, that contribute to the L-Glu binding pocket are also involved in binding of (s)-MCPG. L-Glu, L-Quis and (s)-MCPG wedge into a location adjacent to the $[Ca^{2+}]_o$-binding site in the ECD and maintain the structure of the receptor in its active and resting forms, respectively. The residues with more than one dotted lines indicates those that have more than one oxygen atom contributing to ligand binding. Most of the positive (triangle) and negative (pentagon) (allosteric modulators have been discovered to bind to TMDs but don't share the same binding site.

FIGS. 5A to 5B show effects of CPCCOEt on the responses of mGluR1α to L-Glu and $[Ca^{2+}]_o$. (A) In the presence of 10 or 40 μM CPCCOEt, the sensitivity of mGluR1α to L-Glu was reduced. The maximal response was reduced to about 50% in the presence of 40 μM CPCCOEt. (B) The $[Ca^{2+}]_o$ sensitivity of wild type mGluR1α was reduced by the addition of 5 or 40 μM CPCCOEt. $[Ca^{2+}]_i$ was measured using Fura-2 AM in the absence (solid dots) or presence of 5 μM (solid square) or 40 μM (empty circle) CPCCOEt. In the cells inhibited by CPCCOEt (5 or 40 μM), increasing $[Ca^{2+}]_o$ counteracts the inhibitory effects of CPCCOEt. HEK293 cells transiently expressing WT mGluR1α were mounted on coverslips, and the $[Ca^{2+}]_i$ change indicated by fura-2AM was collected. (N=3).

FIGS. 6A to 6C show $[Ca^{2+}]_o$ and Ro 67-4853 co-activate mGluR1α. HEK293 cells growing on coverslips were transiently transfected with wild type mGluR1α. After dye loading, the cells were pre-incubated in 10 mM HEPES, 140 mM NaCl, 5 mM KCl, 0.55 mM $MgCl_2$, 0.5 mM $CaCl_2$ and 5 nM Ro 67-4853 (pH 7.4) for 10 min. (A) 10 or 100 nM Ro 67-4853 enhances the L-Glu sensitivity of mGluR1α. (B) 30 or 300 nM Ro 67-4853 increases the $[Ca^{2+}]_o$ sensitivity of mGluR1α (C) Addition of $[Ca^{2+}]_o$ and Ro 67-4853 to the cells. Ro 67-4853 displayed activity on mGluR1α in the presence of 0.5 mM $[Ca^{2+}]_o$, while 1.8 mM $[Ca^{2+}]_o$ enhanced its potency.

FIG. 22 is a protein sequence alignment of mGluR1, mGluR2, mGluR3, mGluR4, mGluR5, mGluR6, mGluR7, and mGluR8. The italicized highlighted residues are glutamate binding sites for each mGluRs. The bold residues are calcium binding site1 in mGluR1 (D318, D322 and D325). The bold and underlined are calcium binding site2 (L86-G102). The underlined only parts are calcium binding site3 (S129, G144). The species for mGluRs alignment are from rat and all the sequences are generated from Uniprot.

DETAILED DESCRIPTION

Figure 1B:
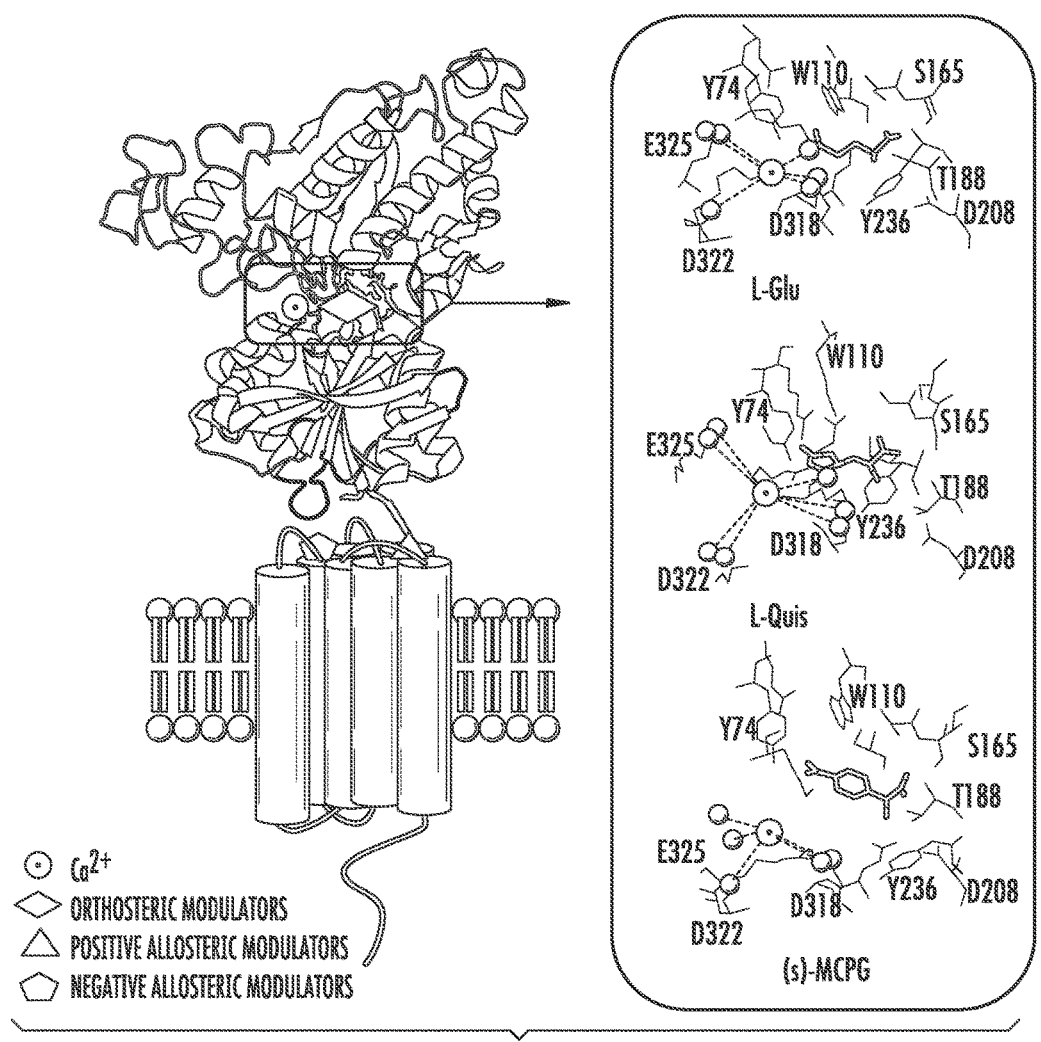

Like other members of the family of C GPCRs, such as the calcium-sensing receptor (CaSR), mGluR1α senses $[Ca^{2+}]_o$ using the extracellular domain (Huang, Y., et al. (2009) Biochemistry 48:388-398; Huang, Y., et al. (2007) J Biol Chem 282:19000-19010). mGluR1-mediated activation of $Ca^{2+}$-activated $Cl^-$ channels is modulated by $[Ca^{2+}]_o$ in addition to L-Glu (Kubo, Y., et al. (1998) Science 279:1722-1725). Purkinje cells from mGluR1 knockout mice lose sensitivity to $[Ca^{2+}]_o$, with this sensitivity to $[Ca^{2+}]_o$ being restored after mGluR1 was genetically reintroduced into the mice (Tabata, T., et al. (2002) Mol Cell Neurosci 20:56-68). There are sparse reports of $[Ca^{2+}]_o$ affecting the action of various classes of compounds acting on mGluRs (Suzuki, Y., et al. (2004) J Biol Chem 279:35526-35534). However, it was not clear how $[Ca^{2+}]_o$ is able to modulate the activity of mGluR1 or the actions of various mGluR1 ligands, and no $Ca^{2+}$-binding sites have been identified in the 15 structures solved by X-ray crystallography to date.

Using a recently developed computational algorithm, a $[Ca^{2+}]_o$-binding site was identified within the hinge region of the ECD of mGluR1α, adjacent to the reported L-Glu-binding site (Wang, X., et al. (2009) Proteins 75:787-798; Wang, X., et al. (2010) Protein science: a publication of the Protein Society 19:1180-1190). It is comprised of D318, E325, D322, and the carboxylate side chain of the natural agonist, L-Glu. The carboxylate side chains of both L-Glu and D318 are involved in both L-Glu- and $[Ca^{2+}]_o$-binding. A mutagenesis study indicated that binding of L-Glu and $Ca^{2+}$ to their distinct but partially-overlapping binding sites synergistically modulates mGluR1α-mediated activation of intracellular $Ca^{2+}$ ($[Ca^{2+}]_i$ signaling. Mutating the L-Glu-binding site completely abolished L-Glu signaling, while leaving its $Ca^{2+}$ sensing capability largely intact. Mutating predicted $Ca^{2+}$-binding residues not only abolished or significantly reduced the sensitivity of mGluR1α to $[Ca^{2+}]_o$ but also, in some cases, to L-Glu (Jiang, Y., et al. (2010) J Biol Chem 285:33463-33474).

The role of $[Ca^{2+}]_o$ in modulating the actions of different orthosteric ligands acting on mGluR1α, including L-Quis, (s)-MCPG, was examined, as well as reciprocal interactions between $Ca^{2+}$ and the mGluR1 allosteric modulators, Ro 67-4853 and CPCCOEt. Predicted $Ca^{2+}$-binding site was found to be adjacent to the orthosteric agonist and antagonist interaction sites and to exhibit a good dynamic correlated motion with these sites as assessed by Molecular Dynamics (MD) simulations. These studies furthermore demonstrated that $[Ca^{2+}]_o$ enhances [$^3$H]-L-Quis binding to wild type mGluR1α and consistently induces $[Ca^{2+}]_i$. Furthermore, these studies indicated that (s)-MCPG efficiently antagonizes both L-Glu- and $[Ca^{2+}]_o$-induced receptor activation at low concentrations, but that increasing the concentration of L-Glu or $[Ca^{2+}]_o$ can overcome this inhibition. In addition, these studies demonstrated that Ro-674853 and CPCCOEt potentiate and inhibit responses to $[Ca^{2+}]_o$, respectively, and $[Ca^{2+}]_o$ increases the potency of Ro-674853 but reduces the inhibition of mGluR1α by CPCCOEt. Therefore, $[Ca^{2+}]_o$ modulates the sensitivity of mGluR1α to not only orthosteric agonists and antagonists but also allosteric modulators, likely by interacting with the predicted $[Ca^{2+}]_o$-binding site in the ECD of the receptor.

Therefore, as disclosed herein, there is a $Ca^{2+}$-binding site in the hinge region of group I mGluRs that is adjacent to the site where orthosteric agonist and antagonist drugs bind on the extracellular domain of the receptor. Moreover, extracellular $Ca^{2+}$ enhances group I mGluR-mediated intracellular $Ca^{2+}$ responses evoked by orthosteric agonists, and diminishes the inhibitory effect of mGluR orthosteric antagonists. In addition, selective positive and negative allosteric modulators of mGluR potentiate and inhibit responses to extracellular $Ca^{2+}$, respectively. Therefore, binding of extracellular $Ca^{2+}$ to the predicted $Ca^{2+}$-binding site in the ECD of mGluR modulates not only glutamate-evoked signaling but also the actions of both orthosteric and allosteric drugs on mGluRs.

Orthosteric and Allosteric mGluR Modulators

To date, eight different mGluR receptor subtypes have been cloned and characterized, and these receptors appear to have diverse neuroanatomical distributions as well as unique pharmacological and intracellular signaling properties. The group I family of mGluRs consists of mGluR1 and mGluR5 receptors, whereas the group II family consists of mGluR2 and mGluR3 and the group III family consists of mGluR4, mGluR6, mGluR7 and mGluR8. The disclosed methods and compositions can involve the use of any orthosteric agonist or antagonist of mGluR that binds in the L-Glu binding pocket of a group I mGluR.

The methods and compositions can also be used with any allosteric modulators that affect the binding of L-Glu to a group I mGluR. Examples of agonists, antagonists, and allosteric regulators of mGluR1 and mGluR5 are set forth in Tables 1A and 1B.

TABLE 1A

Agonists, antagonists, and allosteric regulators of mGluR1

| Ligand | Sp. | Action | Affinity | Units |
|---|---|---|---|---|
| Agonists | | | | |
| [³H]quisqualate | Rn | Full agonist | 7.5-7.7 | pKd |
| quisqualate | Rn | Full agonist | 7.5-8.0 | pKi |
| L-glutamic acid | Rn | Full agonist | 6.4-6.5 | pKi |
| ibotenate | Rn | Full agonist | 5.9-6.4 | pKi |
| (1S,3R)-ACPD | Rn | Full agonist | 5.5-6.1 | pKi |
| 3,5-DHPG | Rn | Full agonist | 5.8 | pKi |
| L-CCG-I | Rn | Full agonist | 5.6 | pKi |
| (S)-3HPG | Rn | Partial agonist | 4.9 | pIC50 |
| Antagonists | | | | |
| AIDA | Hs | Antagonist | 4.2 | pA2 |
| LY341495 | Hs | Antagonist | 7.8 | pKi |
| (S)-4C3HPG | Hs | Antagonist | 5.8-6.0 | pKi |
| LY367385 | Rn | Antagonist | 5.9 | pKi |
| (S)-4CPG | Rn | Antagonist | 5.4 | pKi |
| DCG-IV | Rn | Antagonist | 4.1 | pKi |
| AIDA | Rn | Antagonist | 4 | pKi |
| (+)-MCPG | Rn | Antagonist | 3.8 | pKi |
| 3-MATIDA | Rn | Antagonist | 5.2 | pIC50 |
| LY367385 | Hs | Antagonist | 5.1 | pIC50 |
| (S)-(+)-CBPG | Rn | Antagonist | 4.2 | pIC50 |
| (S)-TBPG | Rn | Antagonist | 4.2 | pIC50 |
| Allosteric Regulators | | | | |
| [3H]R214127 | Hs | Negative | 9 | pKd |
| [3H]EM-TBPC | Rn | Positive | 8.2 | pKd |
| NPS2390 | Rn | Negative | 8.9 | pKi |
| R214127 | Rn | Negative | 8.9 | pKi |
| 9-dimethylamino-3-(4-ethylphenyl)-3H-5-thia-1,3,6-triazafluoren-4-one | Hs | Negative | 8.3 | pKi |
| Ro67-7476 | Rn | Positive | 7.5-7.9 | pKi |
| Ro01-6128 | Rn | Positive | 7.5-7.7 | pKi |
| CPCCOEt | Rn | Negative | 5.3 | pKi |
| Ro67-4853 | Rn | Positive | 5.1 | pKi |
| R214127 | Hs | Negative | 8.9 | pIC50 |
| A841720 | Hs | Negative | 8 | pIC50 |
| 3,5-dimethyl PPP | Rn | Negative | 7.8 | pIC50 |
| DM-PPP | Rn | Negative | 7.8 | pIC50 |
| YM298198 | Rn | Negative | 7.8 | pIC50 |
| BAY 367620 | Rn | Negative | 6.8-8.0 | pIC50 |
| EM-TBPC | Rn | Negative | 6.9 | pIC50 |
| LY456236 | Hs | Negative | 6.9 | pIC50 |
| CPCCOEt | Hs | Negative | 5.2 | pIC50 |

TABLE 1B

Agonists, antagonists, and allosteric regulators of mGluR5

| Ligand | Sp. | Action | Affinity | Units |
|---|---|---|---|---|
| Agonists | | | | |
| quisqualate | Rn | Full agonist | 7.5 | pIC50 |
| L-glutamic acid | Rn | Full agonist | 6.1 | pIC50 |
| L-CCG-I | Rn | Full agonist | 5.8 | pIC50 |
| (1S,3R)-ACPD | Rn | Full agonist | 5.7 | pIC50 |
| ibotenate | Rn | Full agonist | 5.7 | pIC50 |
| 3,5-DHPG | Rn | Partial agonist | 5.4 | pIC50 |
| (S)-3HPG | Rn | Partial agonist | 5 | pIC50 |
| CHPG | Hs | Full agonist | 3.4 | pIC50 |
| Antagonists | | | | |
| ACDPP | Hs | Antagonist | 6.9 | pIC50 |
| (S)-4C3HPG | Rn | Antagonist | 5.6 | pIC50 |
| LY341495 | Hs | Antagonist | 5.1 | pIC50 |
| DCG-IV | Rn | Antagonist | 4.7 | pIC50 |
| (S)-4CPG | Rn | Antagonist | 4.6 | pIC50 |
| (+)-MCPG | Rn | Antagonist | 3.7 | pIC50 |
| Allosteric Regulators | | | | |
| [3H]fenobam | Hs | Negative | 7.5 | pKd |
| [3H]fenobam | Rn | Negative | 7.3 | pKd |
| BOMA | Hs | Negative | 8.5 | pKi |
| MTEP | Hs | Negative | 7.8 | pKi |
| 5-MPEP | Rn | Neutral | 6.4 | pKi |
| VU-1545 | Hs | Positive | 8 | pEC50 |
| CDPPB | Hs | Positive | 7.6-8.0 | pEC50 |
| CDPPB | Rn | Positive | 7.7 | pEC50 |
| MTEB | Hs | Negative | 8.7 | pIC50 |
| [3H]M-MPEP | Hs | Negative | 8.4 | pIC50 |
| [3H]M-MPEP | Hs | Negative | 8.3 | pIC50 |
| [14C]MTEP | Rn | Negative | 7.7 | pIC50 |
| MPEP | Hs | Negative | 7.4-7.7 | pIC50 |
| fenobam | Hs | Negative | 7.2 | pIC50 |
| PTeB | Hs | Negative | 7.2 | pIC50 |
| DFB | Hs | Positive | 5.6-8.5 | pIC50 |
| ADX-47273 | Rn | Positive | 6.5 | pIC50 |
| CPPHA | Hs | Positive | 6.3 | pIC50 |
| SIB-1757 | Hs | Negative | 6.0-6.4 | pIC50 |
| SIB-1893 | Hs | Negative | 5.9-6.5 | pIC50 |

Extracellular Calcium Modulators

The disclosed compositions and methods can involve the use of any agent, regimen, system, or process that can modulate the extracellular levels of calcium near group I mGluR receptors. In particular, the compositions and methods relate to calcium agents that modulate the extracellular levels of calcium in the central or peripheral nervous system, such as in the brain.

In some embodiments, calcium levels are raised by at least 5%, 10%, 15%, 20%, 25%, 30%, 40%, 45%, 50%, 55%, 60%, 65%, 70%, 75%, 80%, 90%, 100%, 200%, or 300% above current levels. In some embodiments, calcium levels are decreased by at least 5%, 10%, 15%, 20%, 25%, 30%, 40%, 45%, 50%, 55%, 60%, 65%, 70%, 75%, 80%, or 90%.

Calcium Supplement

The disclosed calcium agent can be any source of calcium that is capable of raising the free ionized calcium concentration in the plasma to at least 1.0 mmol/L (2.0 mEq/L) in the plasma of a subject. Calcium ($Ca^{2+}$) must be present in a soluble form for efficient absorption from the gastrointestinal tract. This soluble form is generally $Ca^{2+}$ ions, which are hydrated by solvent water or loosely complexed to anionic ligands in solution. Calcium absorption from gastrointestinal tract takes place by both active transport and passive diffusion. The active transport is saturable, stimulated by 1,25-dihydroxyvitamin D3, and predominates in the duodenum and proximal jejunum; while passive transport is the principal mechanism for absorbing large loads of $Ca^{2+}$ (which saturate the active process), and involves the distal jejunum and ileum which have longer transit times.

Many of the studies of $Ca^{2+}$ absorption have employed a single oral dose, ranging from 250 mg up to 2000 mg. With a smaller dose, 15-500 mg of $Ca^{2+}$, the fractional absorption varies inversely with the logarithm of the load size. With a larger load (>500 up to 2000 mg), the fractional absorption increases linearly with load size, reflecting a role of the passive transport over the active transport. Calcium absorption has also been modeled by fitting the amount absorbed to an equation with a hyperbolic term for the saturable process and a linear term for the nonsaturable process.

In some embodiments, the calcium agent can include elemental calcium, calcium salt, and complexed calcium supplements. In various embodiments, the calcium increasing agent is a calcium salt. In some embodiments, the calcium increasing agent can be elemental calcium or a calcium salt or complexed calcium that upon a single and/or multiple administration doses over a period of hours to days, days to weeks, or weeks to months, raises the plasma concentration of free ionized calcium to at least 1.0 mmol/L (2.0 mEq/L) in the subject.

Free ionized calcium is amenable to calculation once the concentration of total plasma calcium concentration is known. The total plasma calcium concentration consists of three fractions. Approximately 15 percent is bound to multiple organic and inorganic anions such as sulfate, phosphate, lactate, and citrate. About 40 percent is bound to albumin in a ratio of 0.8 mg/DI (0.2 mmol/L or 0.4 mEq/L) of calcium per 1.0 g/DI (10 g/L) of albumin. The remaining 45 percent circulates as physiologically active ionized (or free) calcium. The ionized calcium concentration is tightly regulated by parathyroid hormone and vitamin D. The wide range in the normal total plasma calcium concentration is probably due to variations in the plasma concentration of albumin among normal healthy individuals and to variations in the state of hydration and arterial acid-base balance or increased blood concentrations of lactate, citrate and the like in subjects that can alter the albumin concentration and thus the free ionized calcium levels. The net effect is that measurement of the total plasma calcium concentration alone can be misleading, since these parameters can change affecting the ionized calcium fraction.

In some embodiments, the calcium agent can include calcium supplements. The disclosed compositions can also be formulated with one or more calcium supplements by providing sufficient calcium supplement in the composition to reach a predetermined elemental calcium amount for example, from about 100 mg to about 5000 mg, from 100 mg to about 2000 mg, from about 500 mg to about 1,000 mg in the composition.

Neurotransmitter or Amino Acid

In some embodiments, the calcium agent is a neurotransmitter or amino acid that affects sensitivity of the mGluR to calcium. In some embodiments, the calcium agent is a neurotransmitter that promotes calcium release from cellular calcium stores. For example, L-glutamate is a neurotransmitter that can bind with mGluRs to trigger the increase of $IP_3$. $IP_3$ further causes the release of $CA^{2+}$ from the endoplasmic reticulum (ER).

Electric or Mechanical Stimulation

In some embodiments, the calcium agent is an electric or mechanical stimulation. Electrical or mechanical stimulation of neurons causes extracellular calcium to enter cells via channels in the plasma membrane (e.g. voltage gated calcium channel, ligand gated calcium channel). This can increase the average cytosolic calcium concentration from around 100 nM to around 1 µM.

Calcium Sensing

Methods and biosensors for measuring levels of extracellular calcium are known and described, for example, in WO 2012/054648 by Yang et al. and WO 2008/076365 by Yang et al, which are hereby incorporated by reference in their entireties for these teachings. Therefore, in some embodiments, the disclosed methods further involve measuring extracellular $Ca^{2+}$ levels and adjusting the levels of extracellular $Ca^{2+}$ as described above to optimal levels suitable to enhance the activity of one or more group I mGluR orthosteric agonists, orthosteric antagonists, or allosteric modulators. Normal extracellular concentrations of calcium in the brain are in the range from 1.5-2.0 mM range (Jones, H. C., and R. F. Keep. 1987. J. Physiol. (Lond.). 383:441-453). In some embodiments, "optimal levels" of extracellular $Ca^{2+}$ includes levels that are at least 10%, 20%, 30%, 40%, 50%, 60%, 70%, 80%, 90%, 100%, or 200% higher than physiological levels. In particular embodiments, "optimal levels" of extracellular $Ca^{2+}$ includes levels that are at least 50% higher than physiological levels.

Methods of Treatment

The disclosed compositions and methods may be used to treat or prevent any disease or disorder involving dysfunctional group I metabotropic glutamate receptor activity. Metabotropic glutamate receptors have been implicated in a wide range of biological functions. This has suggested a potential role for these receptors in a variety of disease processes in humans or other species.

For example, the disclosed compositions and methods may be used to treat or prevent a variety of neurological and psychiatric disorders associated with glutamate dysfunction, including one or more of the following conditions or diseases: cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; obesity, bulimia nervosa and compulsive eating disorders; pain including bone and joint pain (osteoarthritis), repetitive motion pain, dental pain, cancer pain, myofacial pain (muscular injury, fibromyalgia), perioperative pain (general surgery, gynecological), chronic pain, neuropathic pain, post-traumatic pain, trigeminal neuralgia, migraine and migraine headache; obesity or eating disorders associated with excessive food intake and complications associated therewith; attention-deficit/hyperactivity disorder; conduct disorder; mood disorders including depressive disorders, bipolar disorders, mood disorders due to a general medical condition, and substance-induced mood disorders; muscular spasms and disorders associated with muscular spasticity or weakness including tremors; urinary incontinence; amyotrophic lateral sclerosis; neuronal damage including ocular damage, retinopathy or macular degeneration of the eye, hearing loss or tinnitus; emesis, brain edema and sleep disorders including narcolepsy. Illustrative examples of the neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. The neuropathic pain includes the pain caused by either central or peripheral nerve damage. And it includes the pain caused by either mononeuropathy or polyneuropathy.

In particular, selective pharmacological antagonists and/or negative allosteric modulators of group I mGluRs are potential therapeutic agents for the treatment of numerous disorders of the central nervous system (CNS), including depression, anxiety, drug addiction, chronic pain, Fragile X syndrome (FXS), autism spectrum disorders (ASD), Parkinson's disease, and gastroesophageal reflux disease. Moreover, agonists and positive allosteric modulators (PAMs) of group I mGluRs are potential therapeutic agents for the treatment of other CNS disorders, including schizophrenia, cognitive deficits associated with chronic drug use, and deficits in extinction learning. Therefore, these activities can be enhanced by increasing levels of extracellular $Ca^{2+}$.

Combinations

The disclosed orthosteric antagonists, orthosteric agonists, or allosteric modulators, in combination with calcium agents, may be used in further combination with one or more other therapeutic agents. Such other agents may be administered, by a route and in an amount commonly used therefor, contemporaneously or sequentially with the disclosed compositions. When the disclosed compositions are used contemporaneously with one or more other drugs, a pharmaceutical composition in unit dosage form containing such other drugs and the disclosed compositions is preferred. However, the combination therapy may also include therapies in which the disclosed compositions and one or more other drugs are administered on different overlapping schedules. It is also contemplated that when used in combination with one or more other active ingredients, the disclosed compositions and the other active ingredients may be used in lower doses than when each is used singly. Accordingly, the disclosed pharmaceutical compositions include those that contain one or more other active ingredients, in addition to orthosteric antagonists, orthosteric agonists, or allosteric modulators, in combination with calcium agents.

Therapeutic agents suitable for combination with the disclosed compositions are well known to those with skill in the art, and can be identified by inspection of, inter alia, in Physician's Desk Reference (Medical Economics Company, Montvale, N.J.) and The Merck Index (Merck and Co., Inc., Whitehouse Station, N.J.).

In some embodiments, the disclosed compositions may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In some embodiments, the disclosed compositions may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In some embodiments, the disclosed compositions may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In some embodiments, the disclosed compositions may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In some embodiments, the disclosed compositions may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In some embodiments, the disclosed compositions may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In some embodiments, the disclosed compositions may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, .alpha.-adrenoreceptor antagonists, neurokinin-1 receptor antagonists, atypical antidepressants, benzodiazepines, agonists or antagonists, especially 5-HT.sub. 1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In some embodiments, the disclosed compositions may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine.

Dosage Forms

Also disclosed is a pharmaceutical composition comprising an orthosteric agonist, orthosteric antagonist, or allosteric modulator of one or more mGluRs (referred to collectively herein as "mGluR orthosteric or allosteric drug"). The pharmaceutical composition may optionally also contain the calcium agent. Alternatively, the calcium agent may be present in a second pharmaceutical or nutraceutical composition. The mGluR orthosteric or allosteric drug and/or calcium agent are collectively referred to as "active agents."

The disclosed pharmaceutical compositions may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The disclosed pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The disclosed pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents. Syrups and elixirs may be formulated with sweetening agents, for example glycerol, propylene glycol, sorbitol or sucrose. Such formulations may also contain a demulcent, a preservative, flavoring and coloring agents.

The disclosed pharmaceutical compositions may be in the form of sterile injectable aqueous solutions, micellar formulations or oleaginous suspensions. Suspensions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The mGluR orthosteric or allosteric drug is present in the pharmaceutical composition in a therapeutically effective amount. For example, an appropriate dosage level can be about 0.01 to 500 mg per kg patient body weight per day which can be administered in single or multiple doses. In some embodiments, the dosage level is about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets, capsules, caplets, or pills containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day. This dosage regimen may be adjusted by healthcare providers with knowledge and skill in the art to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Therapeutic Administration

The herein disclosed compositions, including pharmaceutical composition, may be administered in a number of ways depending on whether local or systemic treatment is desired, and on the area to be treated. For example, the disclosed compositions can be administered by oral, parenteral (e.g., intramuscular, intraperitoneal, intravenous, ICV, intracisternal injection or infusion, subcutaneous injection, depot, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Definitions

As used herein, antagonists and agonists of receptors which bind to and are active at only a particular receptor subtype are "selective" agents, whereas those which bind to and are active at more than one receptor subtype are "non-selective." "Orthosteric" ligands are agonists or antagonists which bind to and are active at the primary receptor binding site of a receptor, e.g., the portion of the mGluR receptor to which the endogenous neurotransmitter (glutamate) binds. Orthosteric agents therefore can compete with the neurotransmitter for binding at the primary site, and may be further classified as "competitive" agonists or antagonists. Agonists or antagonists which bind to and are active at a secondary, and in some cases a tertiary, receptor binding site, which are spatially distinct domains for which the endogenous neurotransmitter has very little or no affinity, are termed "allosteric" ligands. These allosteric ligands are "non-competitive" in that, even in high concentration, they will not displace the endogenous ligand by competing for the primary binding site. However, compounds which bind to an allosteric site in a receptor may mitigate, modify, attenuate, enhance, diminish, inhibit, or prohibit the binding of the endogenous neurotransmitter or other orthosteric ligand to the primary binding site. Alternatively compounds which bind to an allosteric site in a receptor may mitigate, modify, attenuate, enhance, diminish, inhibit, or prohibit the physiological function of the activated receptor which include, among others, ion flux regulation, signaling, phosphorylation, and recruitment of proteins. The potency of attraction of an agonist or antagonist, whether orthosteric or allosteric, to its binding site in the receptor, is determined by the sum of non-covalent attractive and repulsive chemical forces of the ligand for the binding site, and is referred to as "affinity". A high affinity agonist or antagonist will bind to its respective site in the receptor at very low concentration, while much higher concentrations of low-affinity molecules are required before significant binding occurs. Agonists or antagonists with sufficient affinity to bind to an allosteric site will produce a dramatic change in the physiological function of an activated mGluR. Such agonists or antagonists are referred to herein as "allosteric modulators" and may exhibit positive (enhanced physiological function) or negative (diminished physiological function) modulation.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "$[Ca^{2+}]_o$" refers to concentrations of extracellular calcium, whereas the term "$[Ca^{2+}]_i$" refers to concentrations of intracellular calcium.

The term "calcium agent" refers to any molecule, regimen, system, or process that can modulate the extracellular levels of calcium near mGluR receptors.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Extracellular Calcium Modulates Actions of Orthosteric and Allosteric Ligands on Metabotropic Glutamate Receptor 1 Alpha Experimental Procedures Dock L-Quis to ECD-mGluR1α Using Autodock-Vina and Hinge Motion Analysis.

To elucidate L-Quis's binding to the ECD of mGluR1α, L-Quis was docked into the crystal structure (1EWK). After removing the coordinates of the bound endogenous ligand, L-Glu, the pdb file was loaded into Autodock tools to add polar hydrogen atoms and choose the docking center and grid box. The docking work was carried out by Autodock tool—Vina (Scripps). The binding residues were analyzed by measuring the atoms within 6 Å of L-Quis. The L-Glu and the (s)-MCPG binding sites within the hinge region were analyzed using Dymdon.

MD Simulation and Correlation Analysis Using Amber.

The initial coordinates for all the simulations were taken from a 2.20 Å resolution x-ray crystal structure with PDBID 1EWK (Kunishima, N., et al. (2000) Nature 407:971-977). The AMBER 10 suite of programs (Case, D. A., et al. (2008) AMBER 10) was used to carry out all of the simulations in an explicit TIP3P water model (Jorgensen, W. L., et al. (1983) J. Chem. Phys. 79:926-935), using the modified version of the all-atom Cornell et. al. (Cornell, W. D., et al. (1995) J. Am. Chem. Soc. 117:5179-5197) force field and the re-optimized dihedral parameters for the peptide ω-bond (Urmi, D., et al. (2009) J. Phys. Chem. 113:16590-16595). The crystal structure contains only PHE substrate. $Ca^{2+}$ ion was placed at the suggested $Ca^{2+}$-binding site that is defined by residues D318, D322, and E325. An initially 2 ns simulation was performed using NOE restraint during the equilibration in order to reorient the side chains residues in the $Ca^{2+}$-binding site, but no restraints were used during the actual simulation. A total of four MD simulations were carried out for 50 ns each on wild type and three mutant mGluRs. The mutations were D318I, D322I, and E325I. First, the structures were minimized to achieve the lowest-energy conformation in each complex. The structures were then equilibrated for 2 ns, starting the MD simulations from the equilibrated structures. During the simulations, an integration time step of 0.002 ps was used to solve Newton's equation of motion. The long-range electrostatic interactions were calculated using Particle Mesh Ewald method (Darden, T., et al. (1993) J. Chem. Phys. 98:10089-10092) and a cutoff of 9.0 Å was applied for non-bonded interactions. All bonds involving hydrogen atoms were restrained using the SHAKE algorithm (Ryckaert, J. P., et al. (1977) J. Comput. Phys. 23:327-341). The simulations were carried out at a temperature of 300 K and a pressure of 1 bar. A Langevin thermostat was used to regulate the temperature with a collision frequency of 1.0 $ps^{-1}$. The trajectories were saved every 500 steps (1 ps). The trajectories were then analyzed using the ptraj module in Amber 10.

Constructs, Site-Directed Mutagenesis, and Expression of mGluR1α Variants.

The red fluorescent protein, mCherry, was genetically tagged to the C-terminal of mGluR1α by a flexible linker—GGNSGG (SEQ ID NO:1) (Jiang, Y., et al. (2010) J Biol Chem 285:33463-33474). Point mutations were introduced using a site-directed mutagenesis kit (Strategene). HEK293 cells were seeded and cultured on glass coverslips. MGluR1α and its mutants were transfected into cells utilizing lipofectamine 2000 (Invitrogen). The cells were then incubated for two additional days, so that mGluR1α and its mutants were expressed at sufficient levels for study. Cells were fixed on the coverslips with 4% formaldehyde, and nuclei were stained with DAPI. The expression of mGluR1α and its variants were detected by measuring red fluorescence using confocal microscopy at 587 nm.

Determining the Effect of $[Ca^{2+}]_o$ on Activation of mGluR1α and its Mutants by L-Quis.

Measurement of $[Ca^{2+}]_i$ was performed as described (Huang, Y., et al. (2007) J Biol Chem 282:19000-19010). In brief, wild type mGluR1α was transiently transfected into the cells and cultured for two additional days. The cells on the coverslips were subsequently loaded using 4 M Fura-2 AM in 2 mL physiological saline buffer (10 mM HEPES, 140 mM NaCl, 5 mM KCl, 0.55 mM $MgCl_2$, 1 mM $CaCl_2$ and pH 7.4) for 30 min. The coverslips were then mounted in a bathing chamber on the stage of a fluorescence microscope at room temperature. Fura-2 emission signals at 510 nm from single cells excited at 340 or 380 nm were collected utilizing a Leica DM6000 fluorescence microscope in real time as the concentration of L-Quis was progressively increased in the presence or absence of $[Ca^{2+}]_o$. The ratio of fluorescence emitted at 510 nm resulting from excitation at 340 or 380 nm was further analyzed to obtain the $[Ca^{2+}]_i$ response as a function of changes in L-Quis. Only the individual cells with mCherry expressed were selected for analysis.

Measurement of $[Ca^{2+}]_i$ Responses of mGluR1α to $[Ca^{2+}]_o$ or L-Glu in the Presence of 0.5 mM s-MCPG.

The methods for measuring $[Ca^{2+}]_i$ responses were as described above. In the presence of (s)-MCPG, the cells were incubated with 0.5 mM (s)-MCPG in a saline buffer for 30 more minutes after Fura-2 loading. Then, the sensitivity of mGluR1α to $[Ca^{2+}]_o$ or L-Glu was measured either by increasing the concentration of L-Glu in the presence of 1.8 mM $[Ca^{2+}]_o$, or by increasing $[Ca^{2+}]_o$ in a stepwise manner in the saline buffer with or without 0.5 mM (s)-MCPG. The L-Glu concentrations were recorded at which the $[Ca^{2+}]_i$ responses of mGluR1α were first observed and then were saturated.

Determining the Effects of $[Ca^{2+}]_o$ on the Potency of Ro 67-4853 on mGluR1α.

Fura-2AM was used for monitoring $[Ca^{2+}]_i$ in real time as described above. Ro 67-4853 did not potentiate mGluR1α in the absence of L-Glu (Hepler, R. W., et al. (2006) Biochemistry 45:15157-15167; Nemeth, E. F., et al. (1998) Proc Natl Acad Sci USA. 95:4040-4045). To obtain the $[Ca^{2+}]_i$ readout, HEK293 cells expressing mGluR1α were pre-incubated with 0.5 mM $Ca^{2+}$ and 5 nM Ro 67-4853 for at least 10 minutes. Cells loaded with Fura-2AM were mounted onto a chamber perfused with saline buffer. By increasing the concentration of Ro 67-4853 stepwise in the presence of 0.5 mM or 1.8 mM $[Ca^{2+}]_o$ $[Ca^{2+}]_i$ was recorded as before by the ratiometric change of fura-2AM in response to changes in $[Ca^{2+}]_i$. The effect of $[Ca^{2+}]_o$ was analyzed by comparing the intracellular $Ca^{2+}$ responses elicited by Ro 67-4853 at two different concentrations of $Ca^{2+}$ in the perfusion buffer. To determine the effect of Ro 67-4853 on the sensitivity of mGluR1α to $[Ca^{2+}]_o$, an additional 30 nM or 300 nM Ro 67-4853 was applied as $[Ca^{2+}]_o$ was increased.

Measurement of $[Ca^{2+}]_i$ Responses of mGluR1α to $[Ca^{2+}]_o$ or L-Glu in the Presence of CPCCOEt.

After the coverslip was mounted in the microscope, the cells were perfused with a saline buffer containing 0, 5 or 40 µM CPCCOEt for more than 10 min. Increasing concentrations of $[Ca^{2+}]_o$ or L-Glu were added to the chamber in the presence of varying concentrations of CPCCOEt, and the $[Ca^{2+}]_i$ response was recorded.

Determining the Effect of $[Ca^{2+}]_o$ on $[^3H]$-L-Quis Binding to mGluR1α and its Mutants.

HEK293 cells transiently transfected with wild type mGluR1α or its mutants were maintained in a 5% $CO_2$ 37° C. incubator for an additional 48 hours as before. Cells were then collected in ice cold hypotonic buffer (20 mM HEPES, 100 mM NaCl, 5 mM $MgCl_2$, 5 mM KCl, 0.5 mM EDTA, and 1% protease inhibitors at pH 7.0-7.5). The cell pellet was washed twice more using hypotonic buffer to remove the L-Glu in the cellular debris. The crude membrane protein (100 µg) was mixed with 30 nM $[^3H]$-L-Quis in 100 µL of hypotonic buffer. The nonspecific binding was determined by measuring bound $[^3H]$-L-Quis in the presence of 200 µM L-Glu. To study the effects of $[Ca^{2+}]_o$ on L-Quis binding to mGluR1α, increasing concentrations of $[Ca^{2+}]_o$ were applied. The reaction mixtures were incubated on ice for at least 1 hour, and the membrane-bound $[^3H]$-L-Quis was captured on filter paper using a Brandel cell harvester under vacuum. The filter paper was then transferred to scintillation fluid, and $[^3H]$-L-Quis was detected using a Beckman LS 6500 multi-purpose scintillation counter.

Results

Predicted $[Ca^{2+}]_o$-Binding Site is Adjacent to Orthosteric Agonist and Antagonist Binding Sites.

Using recently developed computational algorithms, a $Ca^{2+}$-binding site was identified at the hinge region of the ECD of mGluR1α (Jiang, Y., et al. (2010) J Biol Chem 285:33463-33474). FIG. 1 shows that the predicted $Ca^{2+}$-binding site is comprised of D318, E325, D322, and the carboxylate side chain of the natural agonist, L-Glu, in the hinge region in the ECD of mGluR1α, adjacent to the reported L-Glu-binding site. D318 is involved in both L-Glu- and $Ca^{2+}$-binding (Jiang, Y., et al. (2010) J Biol Chem 285:33463-33474).

Using the crystal structure (1EWK, closed-open form) of the receptor's ECD and Autodock-Vina program, the binding site for the orthosteric agonist, L-Quis was modeled. As shown in FIG. 1B, the docked binding site of the agonist, L-Quis, corresponds well with the L-Glu-binding residues previously suggested by the crystal structure. The predicted $Ca^{2+}$-binding site is also adjacent to the L-Quis pocket and interacts with L-Quis similarly to L-Glu (FIG. 1B). In the reported crystal structure of mGluR1 complexed with an orthosteric antagonist, (s)-MCPG (PDBID: 1ISS), (s)-MCPG interacts with Y74, W110, S165, T188, and K409 in lobe one (LB1) and D208, Y236 and D318 in lobe two (LB2) (FIG. 1B) (Tsuchiya, D., et al. (2002) Proc Natl Acad Sci USA. 99:2660-2665). It shares with L-Glu most of the residues of the L-Glu-binding pocket (Tsuchiya, D., et al. (2002) Proc Natl Acad Sci USA. 99:2660-2665) and is also adjacent to the predicted $Ca^{2+}$-binding site.

Figure 2:
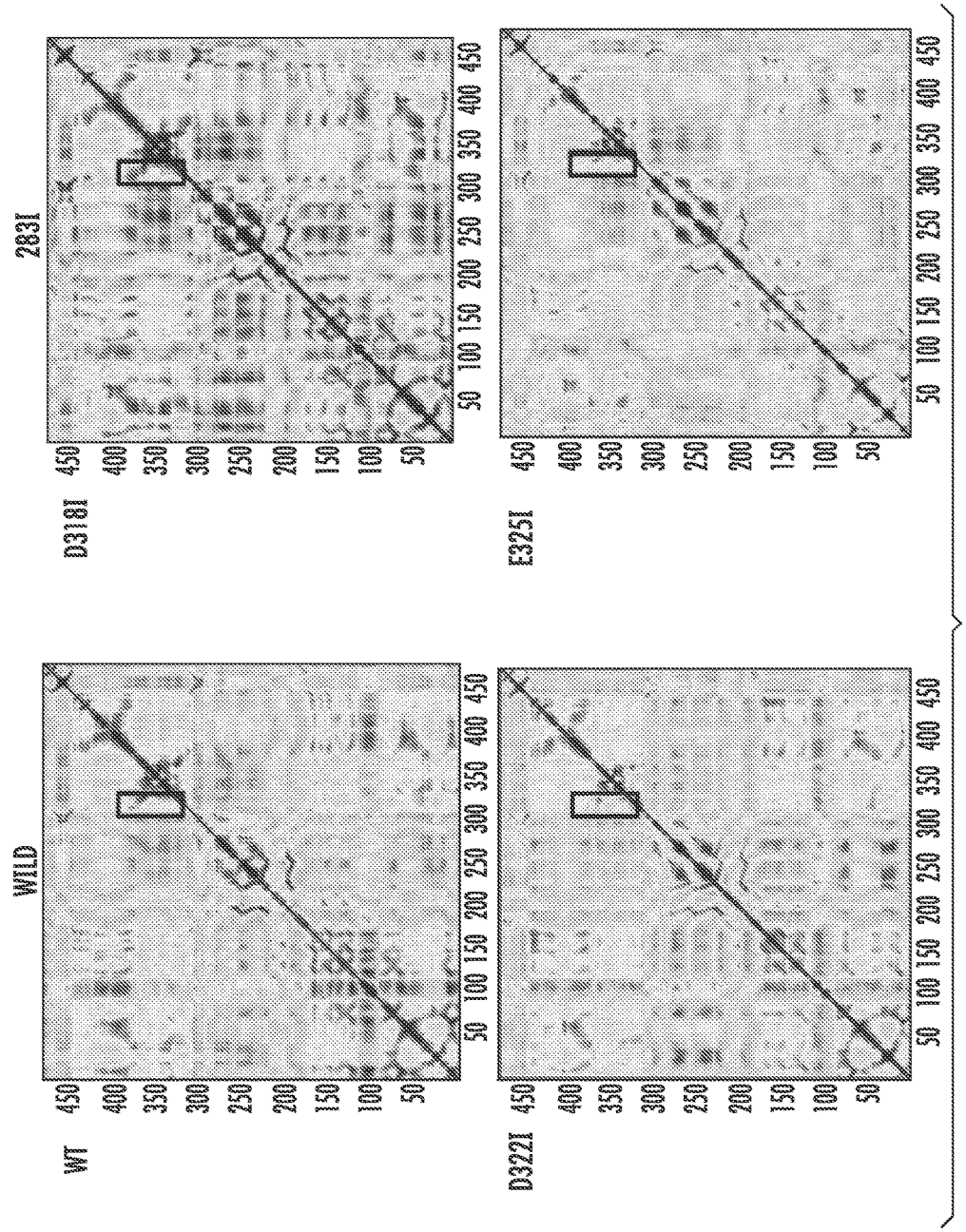
FIG. 2 are correlation maps of WT mGluR1α and D318I, D322I, and E325I. The predicted $[Ca^{2+}]_o$ binding site is well correlated to the L-Glu-binding pocket. Mutations of the $[Ca^{2+}]_o$-binding site impair the correlation to L-Glu binding pocket. The $[Ca^{2+}]_o$-binding site corresponding to the x-axis is highlighted by rectangle.

Molecular Dynamics simulations were next performed to reveal any possible interaction between the predicted $[Ca^{2+}]_o$-binding site and the orthosteric ligand-binding site. Residues involved in the $[Ca^{2+}]_o$-binding pocket, such as D318, D322, and E325, have strong correlated motions, as expected given their roles as $[Ca^{2+}]_o$-binding ligands. In addition, residues D318 and R323 residing within the same loop as the predicted $Ca^{2+}$-binding site are also concurrently correlated. As shown in FIG. 2, most of the critical L-Glu-binding residues, including W110, S165, T188, D208, Y236, D318 and R323, are well correlated to the $[Ca^{2+}]_o$-binding site (D318, D322 and E325). However, mutations at the charged residues involved in $[Ca^{2+}]_o$-binding, such as D318I and E325I, markedly attenuate the correlation of the $Ca^{2+}$-binding site with the L-Glu binding pocket. The $Ca^{2+}$-binding site in mutant D318I only correlates with G293 and D208, and mutant D325I only correlates with Y236 and G293. The mutant D322I also exhibits impaired correlation between the $[Ca^{2+}]_o$-binding site and L-Glu-binding site, but to a lesser degree. As shown in Table 2, D318 in the $[Ca^{2+}]_o$-binding site still correlates with four residues in the L-Glu-binding pocket (FIG. 2). Similarly, residues that are involved in binding L-Quis and (s)-MCPG also correlate well with residues involved in the predicted $[Ca^{2+}]_o$-binding site. Results from these analyses and previous studies on the effect of binding of $[Ca^{2+}]_o$ to its site on L-Glu-mediated activation of mGluR1 indicate that $[Ca^{2+}]_o$ regulates the effects of orthosteric ligands on mGluR1α.

Based on the correlation map shown in FIG. 2, the correlation of reported L-Glu-binding pocket to the $[Ca^{2+}]_o$-binding site (D318, D322 and E325) was observed. The residues with absolute correlation values greater than 0.3 are listed in this table. Of note, WT has five residues (shadowed not included because they resides at the same loop of $[Ca^{2+}]_o$-binding site and would have same motion) in the L-Glu-binding site that correlate with $[Ca^{2+}]_o$-binding 1, while there are only correlations between two residues in variants D318I and E325I, and four in D322I. Bolded residues are in the same loop as the $[Ca^{2+}]_o$-binding site, and they have same movements as the $[Ca^{2+}]_o$-binding site by default.

$Ca^{2+}$ Enhances Sensitivity of Activation of mGluR1α by L-Quis by Increasing [$^3$H]-L-Quis Binding Via Interaction with $[Ca^{2+}]_o$-Binding Site 1 of the Receptor.

Figure 3A:
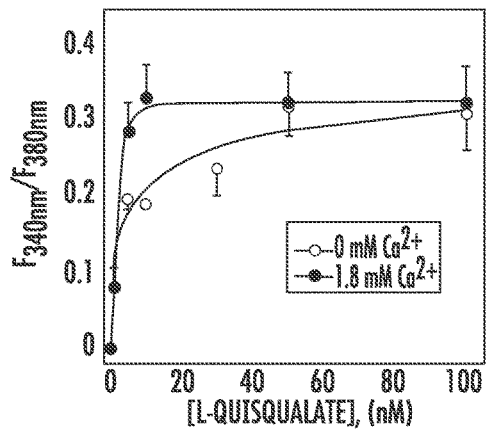
FIGS. 3A to 3E shows extracellular $Ca^{2+}$ enhances L-Quis activation of mGluR1α by binding to the predicted $[Ca^{2+}]_o$-binding site. (A-C) Addition of 1.8 mM $[Ca^{2+}]_o$ (solid dot) increases the L-Quis-induced $[Ca^{2+}]_i$ responses mediated by activation of mGluR1α. The response with 0 mM $[Ca^{2+}]_o$ is indicated by the empty circles. In the presence of 1.8 mM $[Ca^{2+}]_o$, the L-Quis sensitivity of D322I was increased. 1.8 mM $[Ca^{2+}]_o$ also enhanced the potency of L-Quis on E325I. (D) The fold-change in $EC_{50}$ for activation of WT mGluR1α, D322I and E325I by L-Quis upon increasing $[Ca^{2+}]_o$ from nominal zero to 1.8 mM. The-fold decreases in the $EC_{50}$ values for WT mGluR1α, D322I and E325I are 4.6, 3.9 and 2.7, respectively. (E) [$^3$H]-L-Quis binds to WT mGluR1α in the absence of $[Ca^{2+}]_o$, but mutations in the $[Ca^{2+}]_o$-binding site decrease L-Quis-binding. D318I eliminates L-Quis-binding, while D322I and E325I still retain L-Quis binding. An additional 5 mM $[Ca^{2+}]_o$ enhanced L-Quis binding to WT mGluR1α (p=0.031) and D322I, whereas this $[Ca^{2+}]_o$ effect was abolished in E325I. The binding buffer used was hypotonic buffer (N=3). (*p<0.05)
Figure 3B:
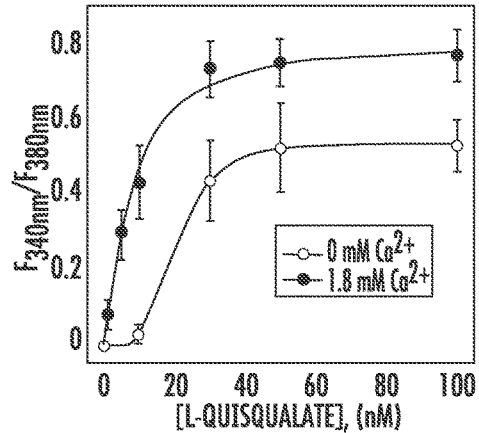
Figure 3C:
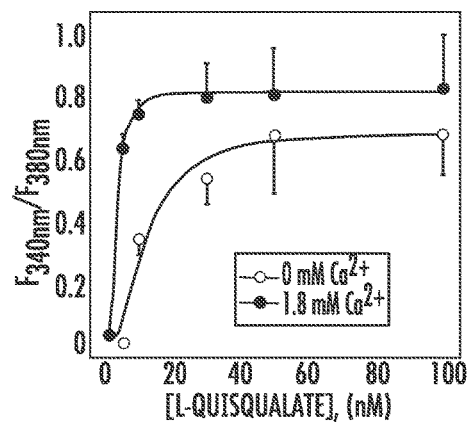
Figure 3D:
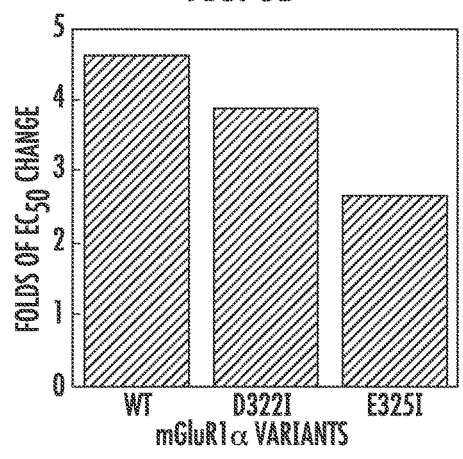

To test the effect of $[Ca^{2+}]_o$ on the activation of mGluR1α by the orthosteric agonist, L-Quis, a single cell fluorescence imaging assay was performed by measuring changes in $[Ca^{2+}]_i$ using HEK293 cells transiently transfected with mGluR1α and loaded with fura-2. To eliminate of the potential effect of trace L-Glu secreted from cells, experiments were conducted using continuous superfusion of cells. FIG. 3A-D show that L-Quis induces intracellular calcium responses mediated by mGluR1 in a similar manner to the activation of the receptor by L-Glu. $[Ca^{2+}]_o$ behaves as a PAM of the L-Quis response and induces a leftward shift in the L-Quis CRC (concentration-response curve) for activation of mGluR1α (FIG. 3A-D). In the absence of $[Ca^{2+}]_o$ ($Ca^{2+}$-free buffer with less than 2 μM calcium), the $EC_{50}$ for the activation of mGluR1a by L-Quis is 12.8 nM. The addition of 1.8 mM $[Ca^{2+}]_o$ reduces the $EC_{50}$ of L-Quis to 2.8 nM (about 4.6 fold) (FIG. 3D, Table 3). This $[Ca^{2+}]_o$-mediated increase in the potency of L-Quis is similar to the effect of $[Ca^{2+}]_o$ on the activation of mGluR1 by its natural agonist, L-Glu (Jiang, Y., et al. (2010) J Biol Chem 285: 33463-33474).

TABLE 2

Mutations in the $[Ca^{2+}]_o$-binding site perturb the correlated motions between the $[Ca^{2+}]_o$-binding site and the L-Glu-binding site

|  | D318 | D322 | E325 |
|---|---|---|---|
| WT | W110, S165, T188, D208, Y236, D318, R323 | W110, S165, T188, Y236, D318, R323 | R323 |
| D318I | D208, G293, D318, R323 | G293, D318, R323 | G293, D318, R323 |
| D322I | Y74, W110, G293, D318, R323, K409 | D318, R323 | Y74, G293, D318, R323 |
| E325I | Y236, G293, D318, R323 | G293, D318, R323 | G293, D318, R323 |

TABLE 3

Effects of $[Ca^{2+}]_o$ on the responses of WT-mGluR1α and variants with mutations $[Ca^{2+}]_o$-binding site 1 to L-Quis. $[Ca^{2+}]_i$ response increase induced by increasing L-Quis via WT- mGluR1a, D322I and E325I were measured in both $Ca^{2+}$ free saline and buffer with physiological $Ca^{2+}$.

| | WT | | | D322I | | | E325I | | |
|---|---|---|---|---|---|---|---|---|---|
| $[Ca^{2+}]_o$ concentration (mM) | $EC_{50}$ (nM) | Maximal Response (%)$^a$ | Fold decrease in $EC_{50}$ | $EC_{50}$ (nM) | Maximal Response (%)$^a$ | Fold decrease in $EC_{50}$ | $EC_{50}$ (nM) | Maximal Response (%)$^a$ | Fold decrease in $EC_{50}$ |
| 0 | 12.8 | 37 ± 4 | 4.6 | 12.4 | 80 ± 16 | 3.9 | 20.6 | 60 ± 8 | 2.7 |
| 1.8 | 2.8 | 37 ± 5 | | 3.2 | 96 ± 21 | | 7.6 | 88 ± 8 | |
| $K_D$ (mM)$^b$ | | 0.3 | | | 0.6 | | | >20.0 | |

$^a$The maximal responses are normalized to the maximal response of WT mGluR1α to L-Glu
$^b$$[Ca^{2+}]_o$-binding affinity of mGluR1α in the presence of 30 nM [$^3$H]-L-Quis (E325I with 300 nM [$^3$H]-L-Quis)

To test whether this $[Ca^{2+}]_o$-mediated increase in the potency of L-Quis occurs via the predicted $[Ca^{2+}]_o$-binding site in the ECD of the receptor, three mGluR1 variants were examined with mutations around the $[Ca^{2+}]_o$-binding site adjacent to the orthosteric binding site at the hinge region. The negatively charged side chain of E325 is important for $[Ca^{2+}]_o$-binding by mGluR1 and not directly involved in L-Glu-binding (Jiang, Y., et al. (2010) J Biol Chem 285:33463-33474). Removal of the $[Ca^{2+}]_o$-binding ligand residue in the mGuR1 variant E325I reduces potency, increasing the $EC_{50}$ from 12.6 to 20 nM in the absence of $[Ca^{2+}]_o$ (FIG. 3D and Table 3). Importantly, this mutation significantly reduces the $[Ca^{2+}]_o$-mediated enhancement in potency for L-Quis from 4.6-fold to 1.6-fold in 1.8 mM $[Ca^{2+}]_o$, although both the potency and efficacy of L-Quis-mediated activation of the E325I mutant are still enhanced relative to WT mGluR1 (FIG. 3A-D). On the other hand, mutant D322I exhibits WT-like behavior in its response to L-Quis both in the absence and presence of $[Ca^{2+}]_o$ (FIG. 3A-D, Table 3), consistent with D322 contributing to $[Ca^{2+}]_o$-binding to a lesser degree, with only its main chain oxygen serving as a ligand atom. WT-like modulation of the L-Glu response of D332I by $Ca^{2+}$ was also observed (Jiang, Y., et al. (2010) J Biol Chem 285:33463-33474). These $[Ca^{2+}]_i$ imaging data suggest that $[Ca^{2+}]_o$ plays a key role in modulating the activation of mGluR1α by L-Quis, possibly via interaction of $[Ca^{2+}]_o$ at the predicted $[Ca^{2+}]_o$-binding site.

Figure 3E:
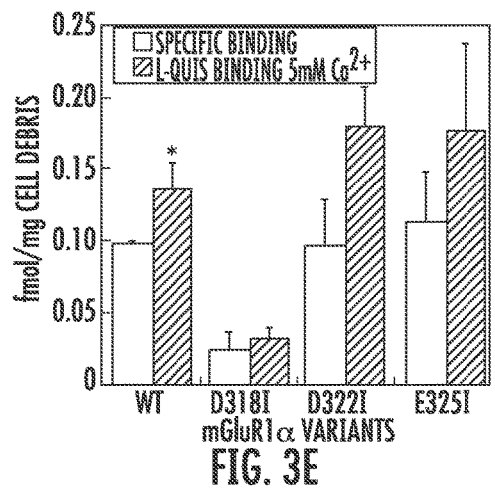
Figure 4A:
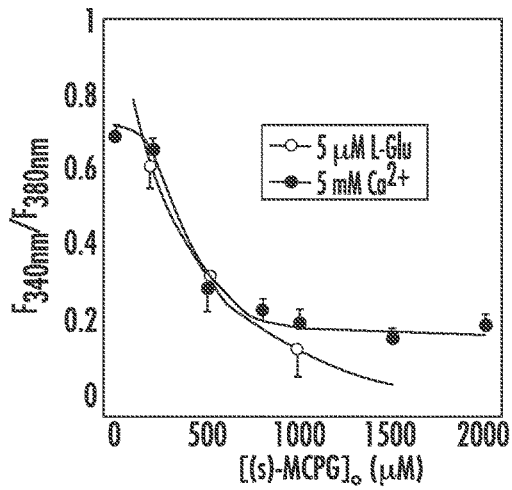
FIGS. 4A to 4C show effects of (s)-MCPG on the response of WT mGluR1α to L-Glu and $[Ca^{2+}]_o$. (A) Increasing the concentration of (s)-MCPG inhibits mGluR1α in the presence of 5 μM L-Glu, and 1.5 mM (s)-MCPG entirely blocks the activation of the receptor by L-Glu. (s)-MCPG attenuates the responsiveness of mGluR1α to 5 mM $[Ca^{2+}]_o$, and 2.0 mM MCPG does not completely inhibit the capacity of the receptor to sense $[Ca^{2+}]_o$. (B) 0.5 mM (s)-MCPG competitively inhibits L-Glu-induced $[Ca^{2+}]_i$ responses. Lineweaver-Burk plot analysis indicates (s)-MCPG competes with L-Glu (inset). (C) 0.5 mM (s)-MCPG inhibits low $[Ca^{2+}]_o$-induced $[Ca^{2+}]_i$ responses, but high $[Ca^{2+}]_o$ restores the response of the receptor. (N=3).
Figure 4B:
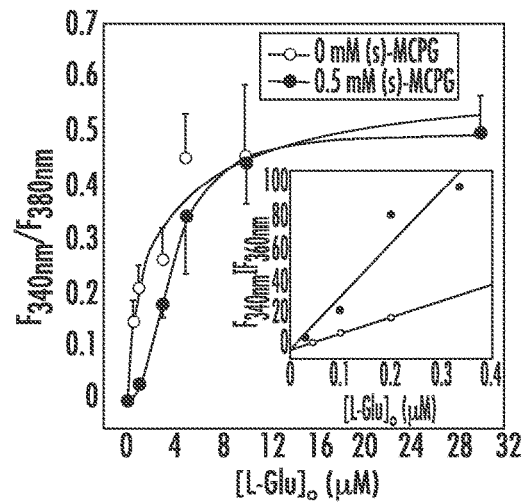

A direct binding assay with radioactive L-Quis ($[^3H]$-L-Quis) was used to assess the impact of $[Ca^{2+}]_o$ on the binding of $[^3H]$-L-Quis to mGluR1α or its variants with mutations at the predicted $[Ca^{2+}]_o$-binding ligand residues in the absence or presence of $[Ca^{2+}]_o$. L-Quis binds to the wild type receptor expressed in HEK293 with a $K_D$ in the range of 30 nM. L-Glu reduces L-Quis binding by competing for the similar orthosteric binding pocket (FIGS. 1B, 4B Insert). $[Ca^{2+}]_o$ significantly enhances L-Quis-binding to the wild type receptor with an $EC_{50}$ in the range of 0.3 mM (FIG. 3E, Table 3). Variant E325I, with removal of negative charge on the key $[Ca^{2+}]_o$-binding residue E325, abolishes L-Quis binding, and this effect is not influenced by the addition of L-Glu or $[Ca^{2+}]_o$ ($K_d$>20 mM) (Table 3). On the other hand, variant D322I retains the binding properties of the wild type receptor for L-Quis suggesting its less essential role in L-Quis binding (FIG. 3E), which is consistent with its role in activation of increases in $[Ca^{2+}]_i$ described earlier. Taken together, both the studies of $[Ca^{2+}]_i$ responses and L-Quis-binding suggest that $[Ca^{2+}]_o$ enhances the activation of mGluR1 by L-Quis by directly modulating binding of L-Quis to mGluR1 through an interaction with predicted $[Ca^{2+}]_o$-binding site 1 in the hinge region.

(s)-MCPG Reduces the Sensitivity of mGluR1α to L-Glu and $[Ca^{2+}]_o$.

The effects of $[Ca^{2+}]_o$ on various mGluR1 ligands acting by different mechanisms on mGluR1 were evaluated using L-Glu as the orthosteric agonist, since it is the physiological activator of the receptor in vivo. As shown in FIG. 4, (s)-MCPG induces a concentration-dependent decrease in the L-Glu-evoked $[Ca^{2+}]_i$ response (FIG. 4A). A concentration of 0.5 mM (s)-MCPG elicits a parallel rightward shift in the L-Glu CRC, and increases the $EC_{50}$ for L-Glu from 1.7 to 3.7 μM. This is consistent with the known action of MCPG as a competitive antagonist at the orthosteric L-Glu binding site.

Figure 4C:
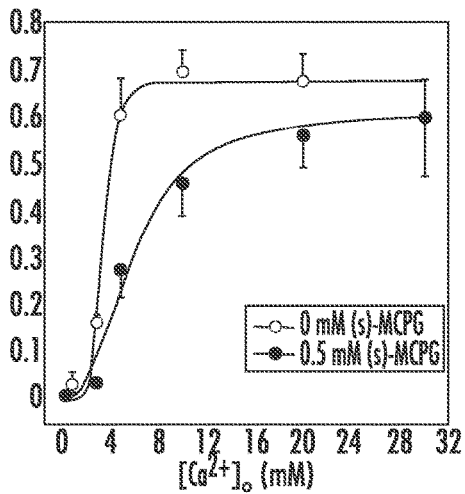

Interestingly, FIG. 4A shows that MCPG also induces a concentration-dependent inhibition of the 5 mM $[Ca^{2+}]_o$-induced $[Ca^{2+}]_i$ response, even in the absence of added L-Glu. Unlike the effect of MCPG on the response to L-Glu, MCPG does not completely block the response to $[Ca^{2+}]_o$. This is consistent with the hypothesis that MCPG inhibits the response to $[Ca^{2+}]_o$ by acting at a site distinct from the one that allosterically regulates the response to $[Ca^{2+}]_o$. MCPG also induces a rightward shift in the $[Ca^{2+}]_o$ CRC. The $EC_{50}$ for $[Ca^{2+}]_o$ increases by ~1.7 fold (from 3.5 to 6.0 mM at 0 and 0.5 mM MCPG, respectively) (FIG. 4C, Table 4). The maximal response to $[Ca^{2+}]_o$ was not affected by 0.5 mM MCPG. However, as noted above, higher concentrations of MCPG could not fully block the maximal effect of 5 mM $[Ca^{2+}]_o$.

TABLE 4

Addition of 0.5 mM (s)-MCPG decreases the responses of mGluR1α to $[Ca^{2+}]_o$ and L-Glu. The $[Ca^{2+}]_i$ response to $[Ca^{2+}]_o$ and L-Glu in the absence or presence of 0.5 mM (s)-MCPG were obtained by measuring the ratiometric change of Fura-2 AM fluorescence.

| | Response to $[Ca^{2+}]_o$ | | | Response to L-Glu | |
|---|---|---|---|---|---|
| (s)-MCPG | $EC_{50}$ (mM) | $n_{Hill}$ | Maximal Response[a] | $EC_{50}$ (μM) | Maximal Response[a] |
| 0 | 3.5 | 6.4 | 85 ± 2 | 1.7 | 100 ± 2 |
| 0.5 | 6.0 | 2.6 | 67 ± 2 | 3.7 | 97 ± 5 |

[a]The maximal responses are normalized to the maximal response of WT mGluR1α to L-Glu NAM CPCCOEt Noncompetitively Inhibits Both L-Glu-Induced and $[Ca^{2+}]_o$-Induced Activation of mGluR1α.

CPCCOEt is known as a selective, non-competitive negative allosteric modulator (NAM) of mGluR1 that binds to residues T815 and A818 in the 7th TMD of the receptor (Harrington, P. E., et al. (2007) Current medicinal chemistry 14:3027-3034) (FIG. 1). As shown in FIG. 5A, the L-Glu-triggered $[Ca^{2+}]_i$ response is significantly depressed in the presence of 5 and 40 μM CPCCOEt. In the presence of 40 μM CPCCOEt, the maximal response decreases to only about half of the control level, while the $EC_{50}$ value increases from 1.7 to 10.1 μM (FIG. 5A, Table 5). To determine the effects of CPCCOEt on the activation of mGluR1α by $[Ca^{2+}]_o$, the effect of CPCCOEt on $[Ca^{2+}]_o$-induced $[Ca^{2+}]_i$ responses was examined. FIG. 5B reveals that CPCCOEt significantly inhibits the $[Ca^{2+}]_o$ sensitivity of mGluR1α. In the presence of 5 μM CPCCOEt, the $EC_{50}$ of mGluR1α for $[Ca^{2+}]_o$ was increased from 3.5 to 14.7 mM. A concentration of 40 μM CPCCOEt produces an even higher $EC_{50}$ value of 28.7 mM (FIG. 5B, Table 5). The maximal response is also significantly decreased by 40 μM CPCCOEt, although the maximal response with 5 μM CPCCOEt is still comparable. This indicates that 30 mM $[Ca^{2+}]_o$ cannot completely reverse the antagonism induced by CPCCOEt, and thus the inhibitory effects of CPCCOEt on the response of mGluR1α to $[Ca^{2+}]_o$ appears to be non-competitive (FIG. 5B, Table 5).

The mGluR1α PAM Ro 67-4853 Potentiates Activation of mGluR1 by $[Ca^{2+}]_o$.

The finding that CPCCOEt inhibits activation of mGluR1 by $[Ca^{2+}]_o$ suggests that the CPCCOEt site, in the trans-membrane-spanning domain of mGluR1, and the $[Ca^{2+}]_o$-binding site, in the ECD of the receptor, interact in a manner similar to the interactions between the orthosteric L-Glu binding site and the allosteric CPCCOEt site. Analogous experiments were performed to determine whether the mGluR1 PAM, Ro 67-4853, which binds to the extracellular loops of the TMDs of mGluR1α, (Lavreysen, H., et al. (2003) Molecular pharmacology 63:1082-1093; Litschig, S., et al. (1999) Molecular pharmacology 55:453-461) (FIG.

1B), can also potentiate responses to $[Ca^{2+}]_o$. FIG. 6A shows that L-Glu-induced activation of WT mGluR1α is enhanced by the addition of 10 or 100 nM Ro 67-4853 using single cell $[Ca^{2+}]_i$ imaging. The effects of Ro 67-4853 on the $[Ca^{2+}]_o$ sensitivity of wild type mGluR1α in the absence of L-Glu was then examined. FIG. 6B shows that both 30 and 300 nM Ro 67-4853 enhanced the $[Ca^{2+}]_i$ response induced by $[Ca^{2+}]_o$, reducing the $EC_{50}$ values for $[Ca^{2+}]_o$ from 3.5 mM to 2.1 and 0.7 mM, respectively. As with the effect of Ro 67-4853 on the response to L-Glu, the maximal response to $[Ca^{2+}]_o$ is not changed by Ro 67-4853 (FIG. 6B and Table 6).

TABLE 5

The effects of CPCCOEt on the responsiveness of mGluR1α to L-Glu and $[Ca^{2+}]_o$ (N = 3). WT mGluR1 was incubated with increasing concentrations of $[Ca^{2+}]_o$ with either 0, 5 or 40 nM CPCCOEt (left side) or to increasing concentrations of L-Glu in the presence of the indicated fixed concentrations of CPCCOEt.

| CPCCOEt Conc. (nM) | Response to $[Ca^{2+}]_o$ | | | Response to L-Glu | |
|---|---|---|---|---|---|
| | $EC_{50}$ (mM) | $n_{Hill}$ | Maximal Response (%)[a] | $EC_{50}$ (μM) | Maximal Response (%)[a] |
| 0 | 3.5 | 6.4 | 85 ± 2 | 1.7 | 100 ± 2 |
| 5 | 7.6 | 1.3 | 75 ± 3 | — | — |
| 10 | — | — | — | 5.2 | 44 ± 8 |
| 40 | 14.7 | 1.1 | 60 ± 3 | 10.1 | 30 ± 10 |

[a]The maximal responses are normalized to the maximal response of WT mGluR1α to L-Glu

TABLE 6

$[Ca^{2+}]_o$ effects on modulation of mGluR1α by Ro 67-4853 (N = 3). WT mGluR1 was incubated with increasing concentrations of Ro 67-4583 with either 0.5 or 1.8 mM $[Ca^{2+}]_o$ (left side) or to increasing concentrations of $[Ca^{2+}]_o$ in the presence of the indicated fixed concentrations of Ro 67-4583.

| $[Ca^{2+}]_o$ Conc. | $EC_{50}$[a] | Max. Res.[c] | Ro 67-4853 Conc. | $EC_{50}$[b] | Max. Res.[c] |
|---|---|---|---|---|---|
| 0.5 (mM) | 20.7 (nM) | 50 ± 8 | 0 (nM) | 3.5 (mM) | 85 ± 2 |
| 1.8 (mM) | 10.0 (nM) | 59 ± 4 | 30 (nM) | 2.1 (mM) | 83 ± 6 |
| | | | 300 (nM) | 0.7 (mM) | 83 ± 2 |

[a]Refers to $EC_{50}$ of Ro 67-4853
[b]Refers to $EC_{50}$ of $Ca^{2+}$
[c]The maximal responses are normalized to the maximal response of WT mGluR1α to L-Glu.

Figure 6C:
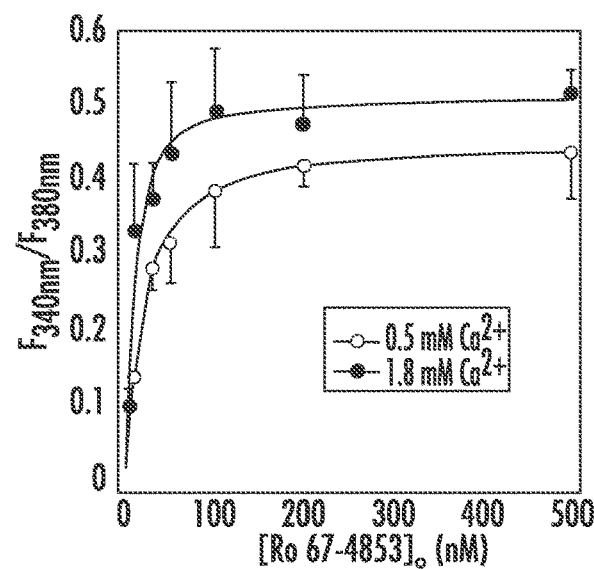

To further evaluate the effect of Ro 67-4853 on mGluR1α, HEK293 cells transiently expressing mGluR1α were preincubated with 0.5 mM $Ca^{2+}$ and 5 nM Ro 67-4853 for up to 10 minutes, and then the responses to multiple concentrations of Ro 67-4853 were tested. In the presence of 0.5 mM $[Ca^{2+}]_o$, Ro 67-4853 enhances L-Glu-induced mGluR1α activity in a concentration-dependent manner. Increasing $[Ca^{2+}]_o$ to 1.8 mM increases the potency of Ro 67-4853 for mGluR1α (FIG. 6C). At the same time, the $EC_{50}$ value decreases from 20.7 to 10.0 nM (FIG. 6C, Table 6). Interestingly, $[Ca^{2+}]_i$ oscillations are observed when the cells are treated with Ro 67-4853. Similar to the $Ca^{2+}$-sensing receptor, three different patterns of response are noted (Huang, Y., et al. (2010) J Biol Chem 285:35919-35931). Most of the cells display a transient spike in $[Ca^{2+}]_i$. Some cells start oscillating after the first peak, while others have a transient peak and oscillations first appear a few minutes later. By analyzing the number of cells oscillating out of the total number of responsive cells, 1.8 mM $[Ca^{2+}]_o$ significantly increases the number of oscillatory cells compared to the cells in 0.5 mM $[Ca^{2+}]_o$. The starting point of oscillation is also shifted leftward. This suggests that $[Ca^{2+}]_o$ enhances the potency of Ro 67-4853 in activating mGluR1α.

Figure 7A:
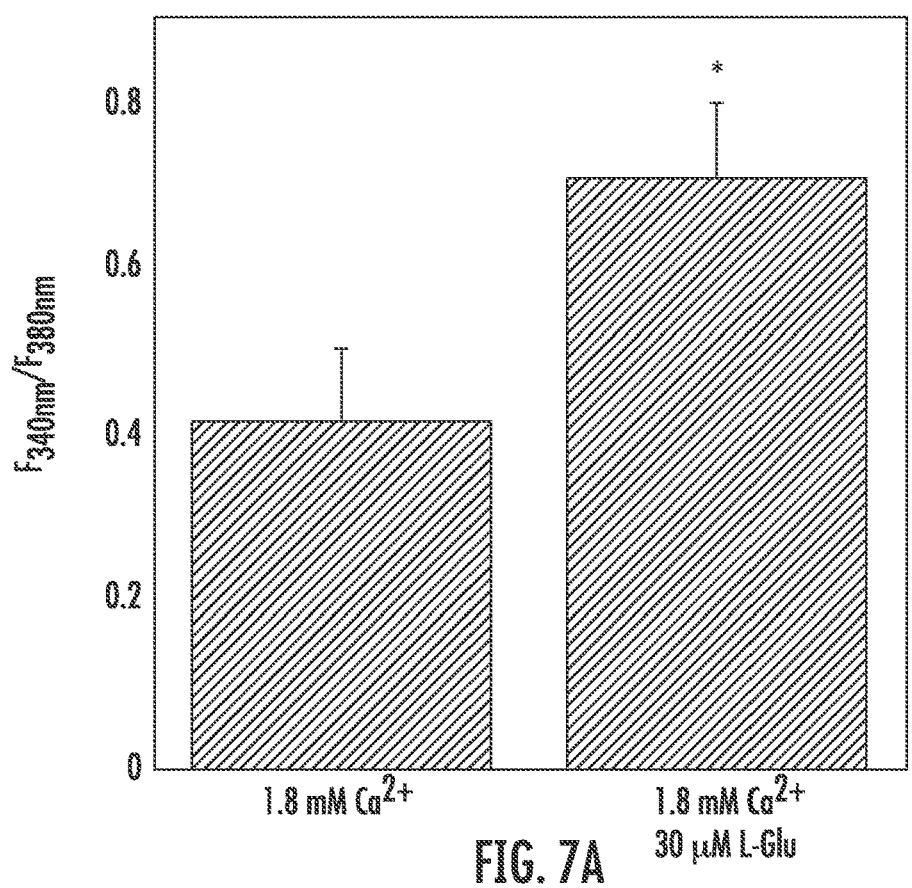
FIGS. 7A and 7B show E325I retains the enhanced responsiveness of the receptor to 10 μM Ro 67-4853 in the presence of L-Glu but loses its potentiation by $[Ca^{2+}]_o$. (A) Addition of 30 μM L-Glu increases the Ro 67-4853 sensitivity of E325I in the presence of 1.8 mM $[Ca^{2+}]_o$ (P=0.014). (B) E325I responds to 10 μM Ro 67-4853 in the absence of both $[Ca^{2+}]_o$ and L-Glu. Increasing $[Ca^{2+}]_o$ from 0 to 5.0 mM had no effect on the response of E325I to Ro 67-4853, while the activity of WT mGluR1 to Ro 67-4853 was progressively enhanced to increases in the $[Ca^{2+}]_i$ response of E325I (N=3) (*p<0.05). Both WT mGluR1 and E325I have stronger responses while exposing to 10 and 20 μM Ro 67-4853 in the presence of 5 mM $Ca^{2+}$, respectively. (*P<0.05)
Figure 7B:
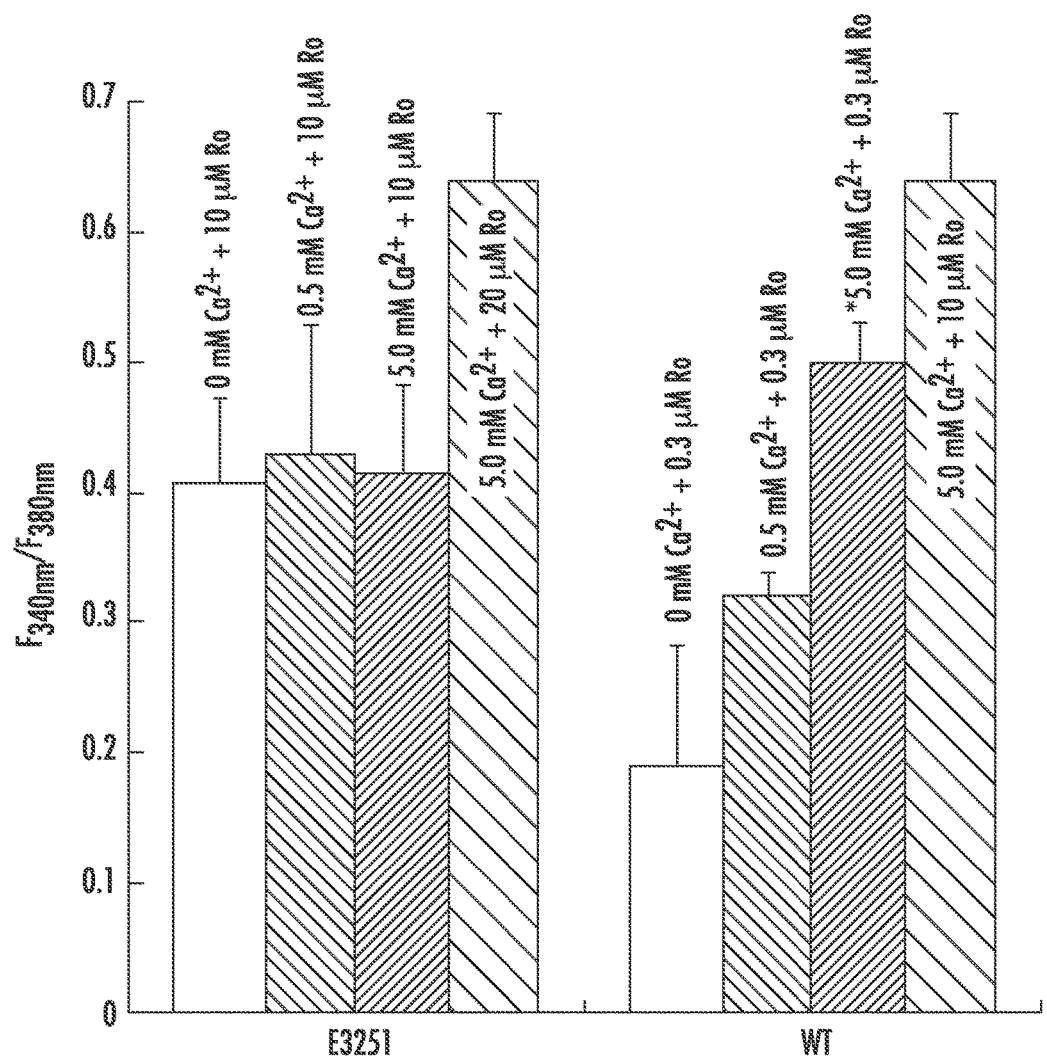

To understand whether this modulation by $[Ca^{2+}]_o$ f the action of this allosteric modulator acting via the TMDs is indeed a result of $[Ca^{2+}]_o$-binding to the predicted $[Ca^{2+}]_o$-binding site 1 in the ECD (e.g., FIG. 1), studies were conducted using an mGluR variant with a key $[Ca^{2+}]_o$-binding ligand residue mutated, E325I. FIG. 1B shows that E325 is not directly involved in L-Glu-binding, and variant E325I is able to sense L-Glu and activate mGluR1α in a manner similar to WT (Jiang, Y., et al. (2010) J Biol Chem 285:33463-33474). FIG. 7A shows that addition of 30 μM L-Glu enhances the responsiveness of E325I to Ro 67-4853. Of note, FIG. 7B shows that E325I responds to 10 μM Ro 67-4853 in the absence of L-Glu in $[Ca^{2+}]_o$-free saline. Increasing $[Ca^{2+}]_o$ from 0 to 5.0 mM does not affect the sensitivity of E325I to Ro 67-4853, but elevating $[Ca^{2+}]_o$ increases the responses of WT mGluR1α to 300 nM Ro 67-4853 (FIG. 7B). This suggests mutating the $Ca^{2+}$ binding site (E325I) eliminates the $Ca^{2+}$ effect on Ro 67-4853, but not WT mGluR1α. To determine if the receptors were saturated by Ro 67-4853, higher concentrations of the PAM were applied to both WT mGluR1 and E325I. As shown in FIG. 7B, higher concentrations of Ro 67-4853 increase the responses of both WT mGluR1 and E325I. This result suggests that $[Ca^{2+}]_o$-binding at its predicted site in the hinge region is essential for the positive allosteric action of this modulator.

Discussion

As disclosed herein, $[Ca^{2+}]$ has significant modulating effects on the actions of various orthosteric and allosteric ligands on mGuR1a, as assessed using a functional readout (i.e., $[Ca^{2+}]_i$ responses) in receptor-transfected HEK293 cells. $[Ca^{2+}]_o$ exerted several different effects on the compounds studied here, including the orthosteric agonist, L-Quis, the orthosteric antagonist, MCPG, and allosteric modulators, e.g., the PAM Ro 67-4853 and the NAM CPCCOEt.

As shown in FIG. 1, the predicted $[Ca^{2+}]_o$-binding site partially overlaps the predicted orthosteric binding site for the agonist, L-Quis, and the antagonist, MCPG. $[Ca^{2+}]_o$ affects $[L-Glu]_o$-induced activation of the receptor. Consistent with this, activation of mGluR1α by L-Quis was enhanced by $[Ca^{2+}]_o$ in a similar manner. Through binding to the $Ca^{2+}$ binding site on ECD-mGluR1, $[Ca^{2+}]_o$ was capable of inducing the hydrolysis of $PIP_2$, thus increasing $IP_3$ and $Ca^{2+}$ release from ER (Jiang, Y., et al. (2010) J Biol Chem 285:33463-33474). $[Ca^{2+}]_o$ was shown to synergistically activate mGluR1α with L-Glu (Jiang, Y., et al. (2010) J Biol Chem 285:33463-33474). However, activation of GPCRs also induces $Ca^{2+}$ influx through store-operated $Ca^{2+}$ entry channels. By utilizing $Gd^{3+}$, an inhibitor of these $Ca^{2+}$ channels, it was noted that mGluR1α still could induce a $[Ca^{2+}]_i$ increase. But comparing this to the $Ca^{2+}$-induced response curve, the $Gd^{3+}$ response brought the curve to the baseline. This suggests that $Ca^{2+}$ release from the ER predominantly induces a transient peak, while $Ca^{2+}$ influx elevates the plateau portion of the response. Increasing $[Ca^{2+}]_o$ enhanced L-Quis binding to HEK293 cells overexpressing mGluR1α, while the mutant E325I abolished this effect of $[Ca^{2+}]_o$ on the activation of mGluR1 (FIG. 3). Moreover, a clear difference in L-Quis and L-Glu binding was observed in the presence of very low $[Ca^{2+}]_o$. Using purified ECD of mGluR1α, Jingami et al. reported that $[Ca^{2+}]_o$ enhances the increase in Trp fluorescence induced by L-Quis and L-Glu (Suzuki, Y., et al. (2004) J Biol Chem 279:35526-35534), although $[Ca^{2+}]_o$ was reported to have no effect on L-Quis binding (Selkirk, J. V., et al. (2001) Neuropharmacology 40:645-656). Nash et al. also observed that $[Ca^{2+}]_o$ produces a higher plateau $[Ca^{2+}]_i$ response and greater $IP_3$ accumulation in CHO cells mediated by mGluR1α (Nash, M. S., et al. (2001) J Biol Chem 276: 19286-19293), although the transient increase in $[Ca^{2+}]_i$ was not affected. Thus, the disclosed observation that $[Ca^{2+}]_o$ enhanced both L-Quis-induced $[Ca^{2+}]_i$ responses and L-Quis binding to the receptor has a physiological implication similar to the modulation by $[Ca^{2+}]_o$ of the action of L-Glu on mGluR1α. FIG. 1 shows that the predicted $[Ca^{2+}]_o$-binding site is located adjacent to the (s)-MCPG binding pocket in mGluR1 in the X-ray structure (PDBID: 1ISS), which is in the hinge region of the ECD and occupies most of the residues involved in L-Glu-binding (Tsuchiya, D., et al. (2002) Proc Natl Acad Sci USA. 99:2660-2665). The effects of gradually increasing concentrations of the orthosteric antagonist, (s)-MCPG, was tested on $[Ca^{2+}]_o$-induced signaling by mGluR1α. As shown in FIG. 4, (s)-MCPG reduced the $[Ca^{2+}]_o$ sensitivity of mGluR1α (FIGS. 4A and C). Increases in the concentrations of either $[Ca^{2+}]_o$ or L-Glu overcame the inhibition induced by (s)-MCPG (FIG. 4). It is interesting to note that (s)-MCPG could not completely block the $[Ca^{2+}]_o$ sensitivity of mGluR1 (FIG. 4C). $[Ca^{2+}]_o$-induced responses mediated by mGluR1α were found to be only partially antagonized by (s)-MCPG (Kubo, Y., et al. (1998) Science 279:1722-1725). (s)-MCPG, was shown to have a capacity to completely inhibit L-Glu-potentiated $Ca^{2+}$-activated $Cl^-$ currents in *Xenopus laevis* oocytes transiently expressing mGluR1 (Kubo, Y., et al. (1998) Science 279:1722-1725). These data indicate that $[Ca^{2+}]_o$ modulates the effects of orthosteric ligands on mGluR.

The observed $[Ca^{2+}]_o$-modulated orthosteric effect is likely dependent on communication of the predicted $[Ca^{2+}]_o$-binding site with the adjacent-binding site for orthosteric agonists and antagonists. The L-Quis binding pocket predicted here using AutoDock-Vina overlaps extensively with the L-Glu-binding pocket in the reported crystal structure (Table 7). The sidechain of D318 is involved in both $[Ca^{2+}]_o$- and agonist-binding. Mutation D318I abrogates both the sensitivity to $[Ca^{2+}]_o$ and responsiveness to L-Glu (Jiang, Y., et al. (2010) J Biol Chem 285:33463-33474). In this study, it also completely eliminated L-Quis-mediated activation of mGluR1 (FIG. 3E). Consistently, mutants T188A, D208A, Y236A and D318A abolished the sensitivity of the receptor to both L-Quis and L-Glu, while the mutants R78E and R78L exhibited clearly impaired L-Quis binding (Levant, J. A., et al. (1973) The New England journal of medicine 289:555-558; Sato, T., et al. (2003) The Journal of biological chemistry 278:4314-4321). The key residue E325 is involved in $[Ca^{2+}]_o$-binding, and the mutant, E325I, indeed significantly impaired both the $[Ca^{2+}]_o$ and L-Glu sensitivity of the receptor (FIG. 3). On the other hand, variant D322I produced less reduction of the modulatory effects of $[Ca^{2+}]_o$ on both L-Quis and L-Glu agonist action and is consistent with its lesser role in $[Ca^{2+}]_o$-binding with a contribution of only a main chain ligand atom (FIG. 1).

TABLE 7

Analysis of ligand interaction by LPC server. PDB files bound with L-Quis, L-Glu and (s)-MCPG were analyzed by online LPC server. The output including distance, surface interacting and atom number contributing to binding were as summarized below.

| Residue Number | Distance (Å) | | | Surface (Å2) | | | Number of contacts | | |
|---|---|---|---|---|---|---|---|---|---|
| | L-Quis | L-Glu | (s)-MCPG | L-Quis | L-Glu | (s)-MCPG | L-Quis | L-Glu | (s)-MCPG |
| Y74 | 2.7 | 2.5 | 2.6 | 29.4 | 37.3 | 46.7 | 9 | 7 | 7 |
| R78 | — | 5.1 | 5.5 | — | 0.3 | 1.6 | — | 1 | 1 |
| W110 | 3.6 | 3.9 | 3.9 | 37.1 | 20.2 | 28.5 | 8 | 8 | 9 |
| G163 | 3.7 | 3.9 | 4.8 | 8.5 | 8.7 | 2.7 | 2 | 2 | 1 |
| S164 | 3.1 | 3.5 | 4.8 | 23.6 | 7.3 | 8.3 | 3 | 3 | 4 |
| S165 | 3.0 | 2.7 | 2.9 | 35.7 | 43.7 | 46.6 | 4 | 4 | 7 |
| S166 | — | — | 4.4 | — | — | 0.7 | — | — | 1 |
| S186 | 3.5 | 2.8 | 3.7 | 26.5 | 29.3 | 27.2 | 5 | 5 | 10 |
| A187 | 3.6 | 3.3 | — | 1.6 | 1.6 | — | 1 | 1 | — |
| T188 | 3.8 | 2.9 | 3.2 | 3.9 | 27.9 | 27.0 | 2 | 4 | 3 |
| S189 | — | — | 5.0 | — | — | 2.7 | — | — | 3 |
| D208 | — | — | 4.8 | — | — | 0.9 | — | — | 2 |
| Y236 | 3.6 | 3.4 | 4.2 | 42.9 | 40.4 | 46.7 | 10 | 14 | 13 |
| E292 | 3.9 | 5.0 | — | 22.2 | 5.0 | — | 7 | 5 | — |
| G293 | 3.7 | 5.1 | — | 25.9 | 1.2 | — | 3 | 1 | — |
| M294 | 4.6 | — | — | 3.3 | — | — | 2 | — | — |
| D318 | 3.7 | 2.8 | 5.0 | 19.8 | 31.3 | 9.5 | 3 | 2 | 4 |
| G319 | 3.4 | 3.7 | 6.2 | 19.2 | 21.4 | 1.3 | 4 | 3 | 2 |
| R323 | 3.5 | 3.7 | 6.1 | 15.5 | 10.4 | 3.1 | 3 | 1 | 1 |
| K409 | 2.8 | 3.6 | 3.1 | 32.2 | 23.9 | 30.0 | 3 | 4 | 4 |

"—" means no contacts

The observed effect of $[Ca^{2+}]_o$ on responses to orthosteric agonists and antagonists of mGluR1 is consistent with Molecular Dynamics studies performed here on the correlated motions of the hinge region in the ECD of mGluR (FIG. 2, Table 2). A strong correlation among residues in the predicted $[Ca^{2+}]_o$-binding site and residues involved in the orthosteric binding sites shared by L-Glu, L-Quis and MGPG were observed. Interestingly, mutation of the $[Ca^{2+}]_o$-binding site largely removed this correlation. FIG. 1A shows that the predicted $[Ca^{2+}]_o$-binding site at the hinge region is conserved in the group I mGluRs, e.g., mGluR1 and mGluR5 (Jiang, Y., et al. (2010) J Biol Chem 285: 33463-33474), calcium-sensing receptor and T1R3, a taste receptor for $[Ca^{2+}]_o$, (Dorr, P., et al. (2005) Antimicrobial agents and chemotherapy 49:4721-4732). In our previous study, $[Ca^{2+}]_o$ exhibits synergy with L-Glu in activating mGluR1α (Jiang, Y., et al. (2010) J Biol Chem 285:33463-

33474). The effect of $[Ca^{2+}]_o$ in modulating orthosteric ligands that act on mGluR via communication at the hinge region of the ECD. Binding of L-Phe and other amino acids to a site in the hinge region of the CaSR likely communicates with the predicted $[Ca^{2+}]_o$-binding site at the hinge region to increase the sensitivity of the receptor to $[Ca^{2+}]_o$ (Huang, Y., et al. (2009) Biochemistry 48:388-398; Huang, Y., et al. (2007) J Biol Chem 282:19000-19010; Conigrave, A. D., et al. (2007) The Journal of nutrition 137:1524S-1527S; discussion 1548S; Zhang, Z., et al. (2002) J Biol Chem 277:33727-33735). In recent years, increasing numbers of family C GPCRs, have been found to exhibit synergistic modulation of the primary orthosteric agonist by allosteric modulators. Sweet enhancers binding to the hinge region of the human taste receptor are known to stabilize the active form of the receptor, thus leading to altered perception of sweet taste, while IMP and L-Glu also synergistically activate the umami taste receptor (Zhang, F., et al. (2010) Proc Natl Acad Sci USA. 107:4752-4757; Zhang, F., et al. (2008) Proc Natl Acad Sci USA. 105:20930-20934). It is also interesting to note that a suggested allosteric ligand acting at the ECD domain of mGluR is located at the hinge region (Acher, F. C., et al. (2011) Neuropharmacology 60:102-107; Ogawa, H., et al. (2010) Protein science: a publication of the Protein Society 19:544-557). Thus, the disclosed evidence has strong implications for the role of the hinge region of the ECD in modulating action of small molecule ligands on family C GPCRs.

As for allosteric modulators targeting the TMDs, the binding sites of positive and negative modulators of mGluR1α are distinct (Hemstapat, K., et al. (2006) Molecular pharmacology 70:616-626). These allosteric modulators effectively modulate receptor activation by L-Glu, but little is known about the effects of the endogenous mineral ion, $Ca^{2+}$, on these modulators. In this study, the effects of $[Ca^{2+}]_o$ on CPCCOEt (NAM) and Ro 67-4853 (PAM) were further assessed.

The non-competitive NAM, CPCCOEt, is known to inhibit the L-Glu response by binding to T815 and A818 on the $7^{th}$ TMD) (Rodriguez, A. L., et al. (2005) Molecular pharmacology 68:1793-1802; Brauner-Osborne, H., et al. (1999) Neuroreport 10:3923-3925). Our data shown in FIG. 5 support the contention that CPCCOEt, acting as a non-competitive inhibitor, also can diminish the $[Ca^{2+}]_i$ response of mGluR1α. Interestingly, increasing $[Ca^{2+}]_o$ restored $[Ca^{2+}]_o$ sensitivity of the receptor. CPCCOEt not only inhibits proliferation of melanoma cells, but also reverses morphine tolerance (Haas, H. S., et al. (2007) The Oncol Rep 17:1399-1404; Smith, F. L., et al. (2004) Eur J Pharmacol 492:137-142). Thus, the findings in this study indicate that a drug targeting the $[Ca^{2+}]_o$-binding site in mGluR1 has the potential to tune the therapeutic effect of CPCCOEt on melanoma or addiction. V757 in the TMD was revealed to be critical to the activation of mGluR1 by the PAMs (Nemeth, E. F., et al. (1998) Proc Natl Acad Sci USA. 95:4040-4045; Hemstapat, K., et al. (2006) Molecular pharmacology 70:616-626). By analyzing the $[Ca^{2+}]_i$ transients and oscillations observed here, $[Ca^{2+}]_o$ not only reduced the concentration of Ro 67-4853 required to initiate $[Ca^{2+}]_i$ oscillations, but also decreased the $EC_{50}$ value and increased the maximal responses of HEK293 cells expressing mGluR1 (FIG. 6 and Table 6). In the presence of Ro 67-4853, the $[Ca^{2+}]_o$ sensitivity of mGluR1α was also enhanced, indicating an allosteric interaction between the $[Ca^{2+}]_o$-binding site and the site for Ro 67-4583. Interestingly, Ro 67-4853 only enhanced activation of mGluR1α by physiological $[Ca^{2+}]_o$ concentrations, while further increases in $[Ca^{2+}]_o$ abolished the Ro 67-4853 effect. This indicates that a change in $[Ca^{2+}]_o$ within the physiological range could serve as a PAM, similar to Ro 67-4853, and suggests that $[Ca^{2+}]_o$-induced enhancement of the potency of Ro 67-4853 may activate mGluR1 via the TMDs, and that the activation of the TMDs could enhance the sensitivity of the receptor to agonist. Since site-directed mutagenesis suggests that Ro 67-4853 along with the other PAMs, Ro 01-6128, and Ro 67-7476, likely share the same binding pocket involving V757. $[Ca^{2+}]_o$ could potentially enhance the potencies of other members of the Ro and VU series.

The observed modulation of the effects of PAM and NAM by $[Ca^{2+}]_o$ can be explained by the integrated action of the ECD domain with the TMDs of the receptor. This is supported by studies using a mutation of a key $[Ca^{2+}]_o$-binding ligand residue, E325I, at the predicted $[Ca^{2+}]_o$-binding site adjacent to the L-Glu-binding site. Variant E325I markedly reduces the modulation of the action of Ro67-4853 by $[Ca^{2+}]_o$ (FIG. 7). PAMs binding to the TMDs have been shown to enhance L-Quis binding to mGluR1α (Nemeth, E. F., et al. (1998) Proc Natl Acad Sci USA. 95:4040-4045). It is possible that the incomplete reduction in the inhibitory effect of MCPG by $[Ca^{2+}]_o$ is due to an additional synergistic effect involving the TMD region of the receptor. By tagging the FRET pair YFP/CFP to the two intracellular loops 2 (i2) of the dimeric mGluR1α, Muto et al. observed that the re-arrangement of the TMD induced by L-Glu was reversed by (s)-MCPG (Tateyama, M., et al. (2004) Nat Struct Mol Biol 11:637-642). Such an integrated effect of the TMDs with the ECD region is further supported by studies of mGluRs with deletions of the VFT. It was found that PAMs not only potentiate the action of agonists on the full-length receptors, but sometimes can display strong agonist activity on VFT truncated receptors (El Moustaine, D., et al. (2012) Proc Natl Acad Sci USA. 109:16342-16347; Goudet, C., et al. (2004) Proc Natl Acad Sci USA. 101:378-383). The VFTs of the ECDs are not only responsible for agonist-induced activation, but also prevent PAMs from activating the full-length receptor (El Moustaine, D., et al. (2012) Proc Natl Acad Sci USA. 109:16342-16347; Goudet, C., et al. (2004) Proc Natl Acad Sci USA. 101:378-383). Taken together, this study reveals that $[Ca^{2+}]_o$-binding at the hinge region is likely to be responsible for its capacity to modulate action of other allosteric modulators. $[Ca^{2+}]_o$ at physiological levels (1.8 mM) enhanced the potency of Ro 67-4853 in modulating mGluR1α, while increasing $[Ca^{2+}]_o$ diminished the inhibitory effects of CPCCOEt (FIGS. 5-7, Tables 5-6). Over the past decade, many new PAMs and NAMs for various receptors have been developed, and the potential exists for developing allosteric modulators with greater subtype specificity than is possible for orthosteric agonists (Wang, L., et al. (2009) J Pharmacol Exp Ther 331:340-348). The co-activation induced by endogenous agonists and PAMs binding to the receptors' hinge regions could be a common feature of family C GPCRs. These data provide further insight into the modulation of mGluR1α by $[Ca^{2+}]_o$ and suggest that $[Ca^{2+}]_o$ has the potential to modulate the profile of a variety of agents acting on mGluR1α, including agonists, antagonists and allosteric modulators.

Example 2

Measurement of $[Ca^{2+}]_i$ Responses of mGluR5 to $[Ca^{2+}]_o$

Methods

HEK293 cells were fed on a Dulbecco's Modified Eagle Medium (DMEM) and 10% fetal bovine serum (Invitrogen)

and cultured at 37° C. in a humidified incubator with 5% $CO_2$. One day before transfection, HEK293 cells were grown on 22×44 mm coverslips and then were transfected with mGluR5 plasmid (received as a gift from Dr. Randy Hall, Emory University, Atlanta, Ga.) with the aid of lipofectamine 2000 (Invitrogen). mGluR5 transfected HEK293 cells were grown for 48 hours and then loaded with 4 M Fura-2 AM in loading buffer containing 10 mM HEPES (pH 7.4), 140 mM NaCl, 5 mM KCl, 0.55 mM $MgCl_2$ for 30 minutes at 37° C. The coverslips were then mounted in a bathing chamber on the stage of a fluorescence microscope. Fura-2 emission signals at 510 nm from single cells excited at 340 or 380 nm were recorded using a Leica DM6000 fluorescence microscope in real time as the $Ca^{2+}$ was progressively increased. The ratio of fluorescence emitted at 510 nm resulting from excitation at 340 or 380 nm was analyzed to obtain the $[Ca^{2+}]_i$ response as a function of changes in $[Ca^{2+}]_o$.

Results

Figure 8:
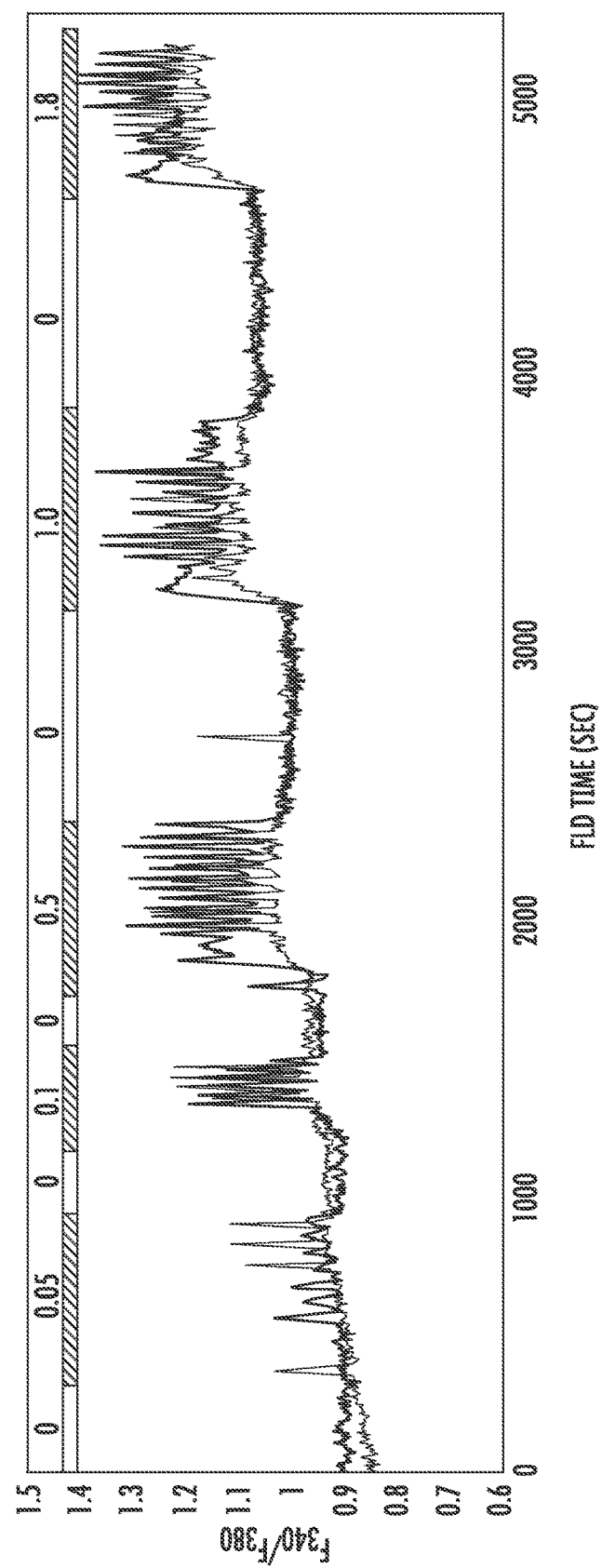
FIG. 8 shows extracellular $Ca^{2+}$ concentration change induced intracellular $Ca^{2+}$ oscillation. Extracellular $Ca^{2+}$ concentration was increased from 0.05 mM to 1.8 mM. $Ca^{2+}$-free bath solution was used to between different $Ca^{2+}$ concentrations to remove the preceding addition.
Figure 9A:
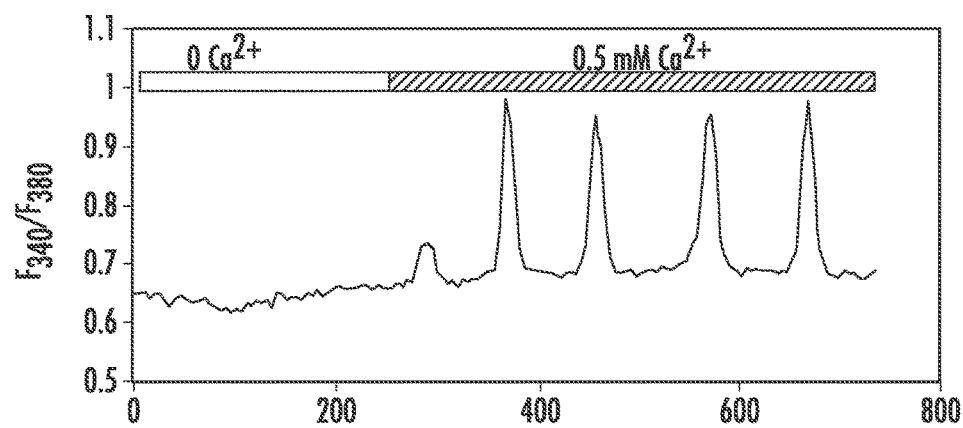
FIG. 9A to 9C shows different extracellular $Ca^{2+}$ concentration resulted in divergent frequency of intracellular $Ca^{2+}$ oscillation.
Figure 9B:
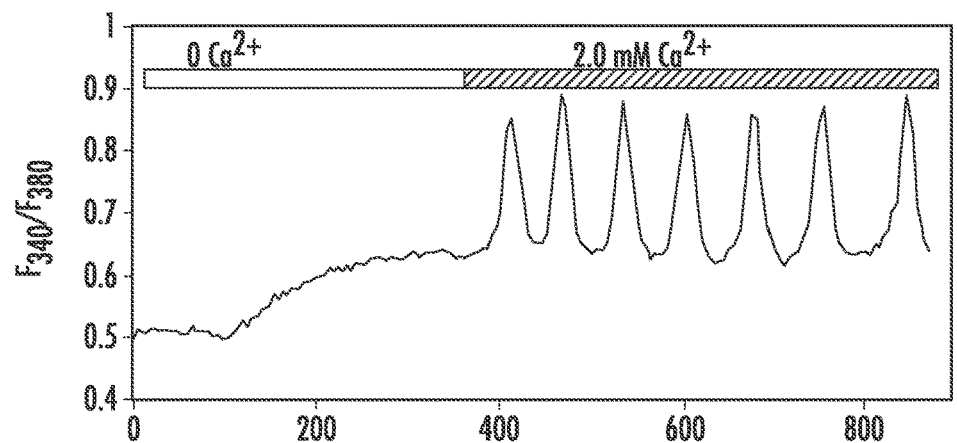
Figure 9C:
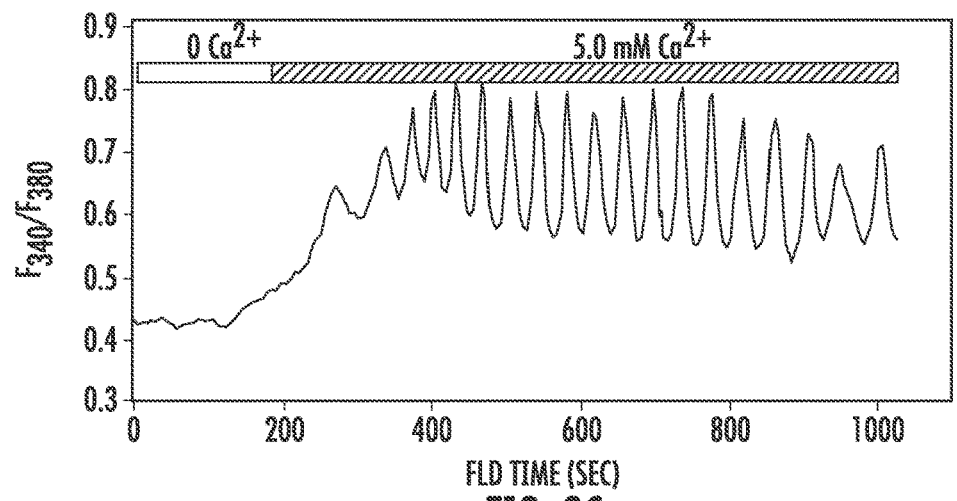
Figure 10:
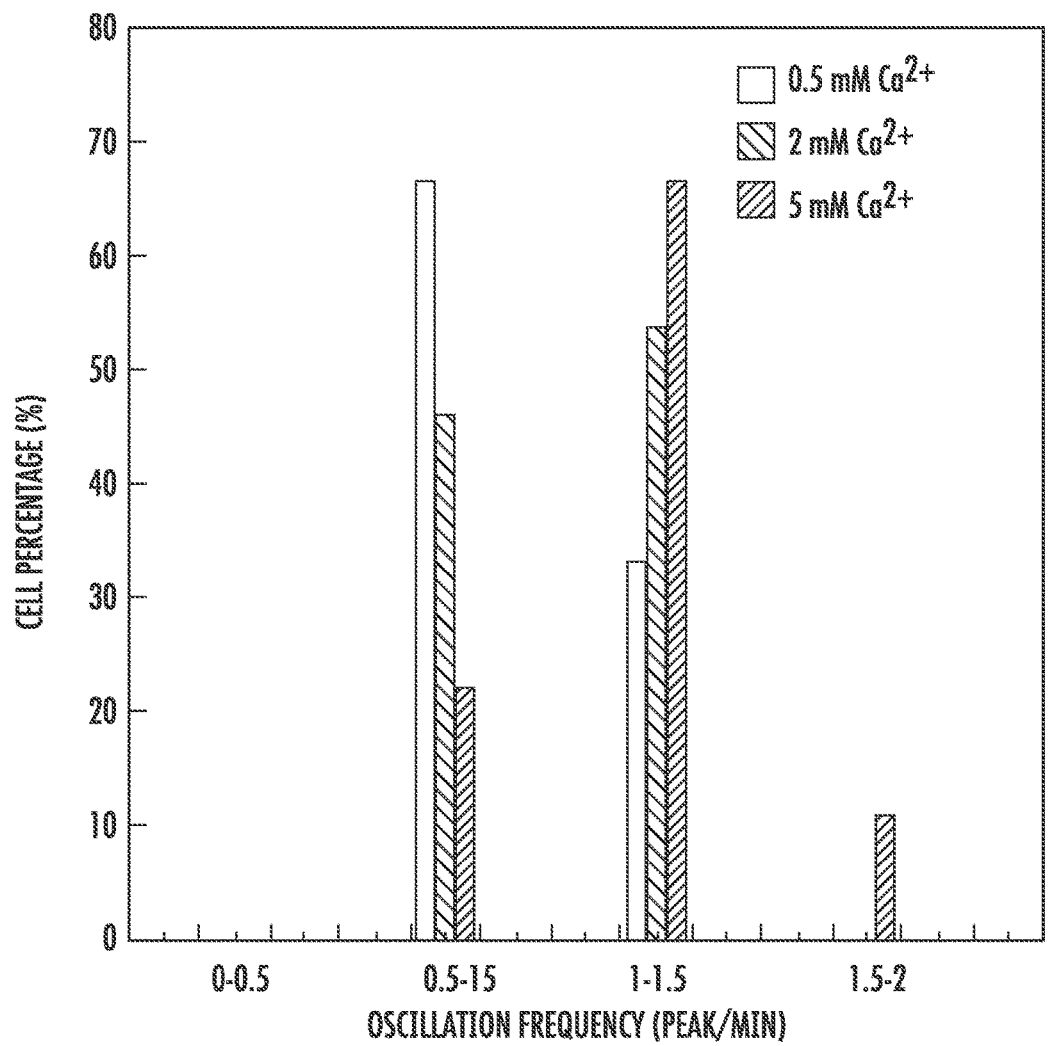
FIG. 10 is a bar graph showing higher extracellular $Ca^{2+}$ concentration triggered faster intracellular $Ca^{2+}$ oscillation in HEK293 cells overexpressing mGluR5.
Figure 11A:
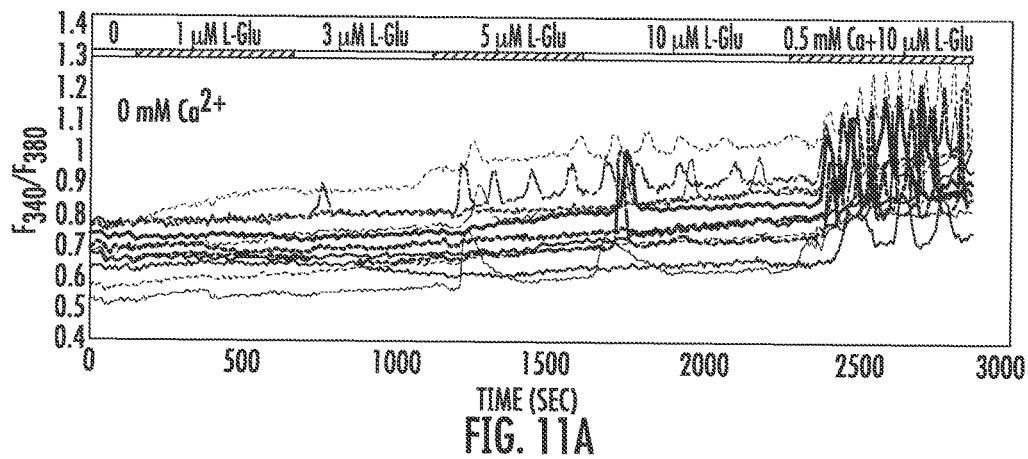
FIGS. 11A to 11C shows mGluR response to L-Glu in the presence of 0.0 mM (FIG. 11A), 0.5 mM (FIG. 11B), and 1.8 mM (FIG. 11C) extracellular $Ca^{2+}$. In the absence of $Ca^{2+}$, higher dosage of L-Glu is required to activate mGluR5, while lower L-Glu can activate the mGluR5 if extracellular is applied.
Figure 11B:
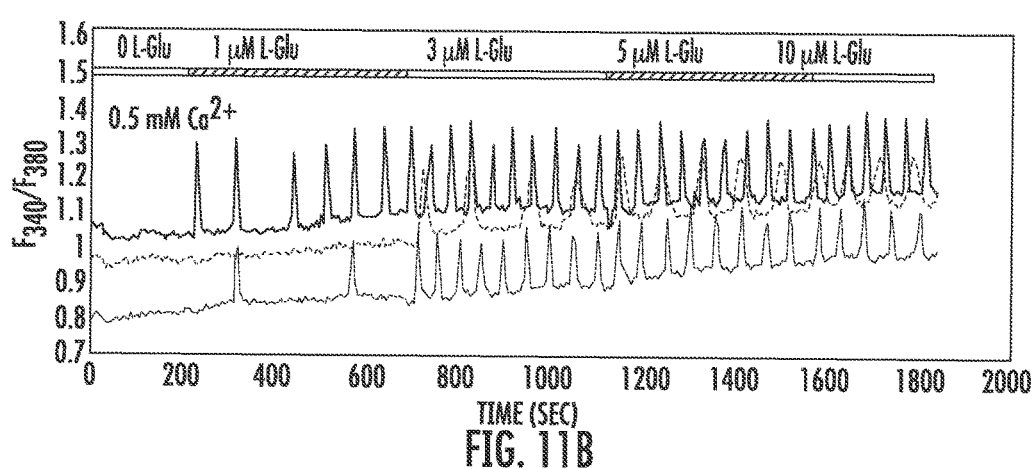
Figure 11C:
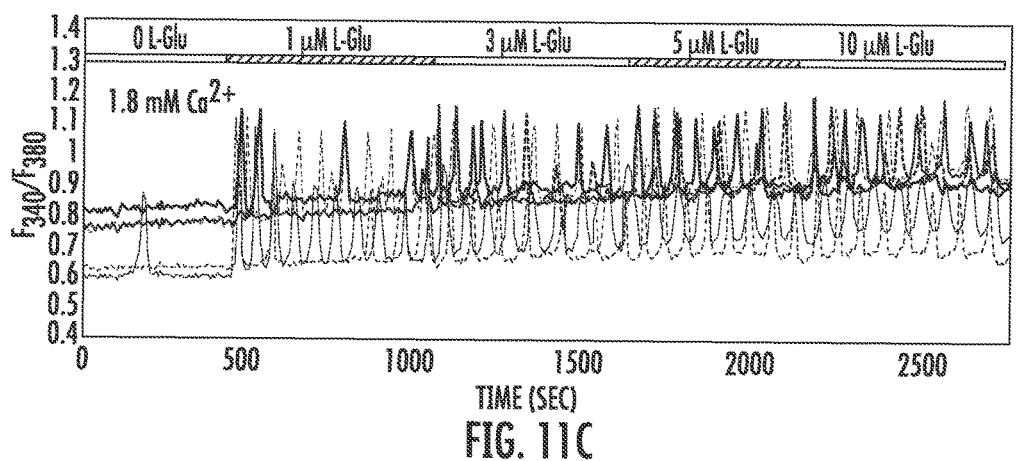
Figure 12:
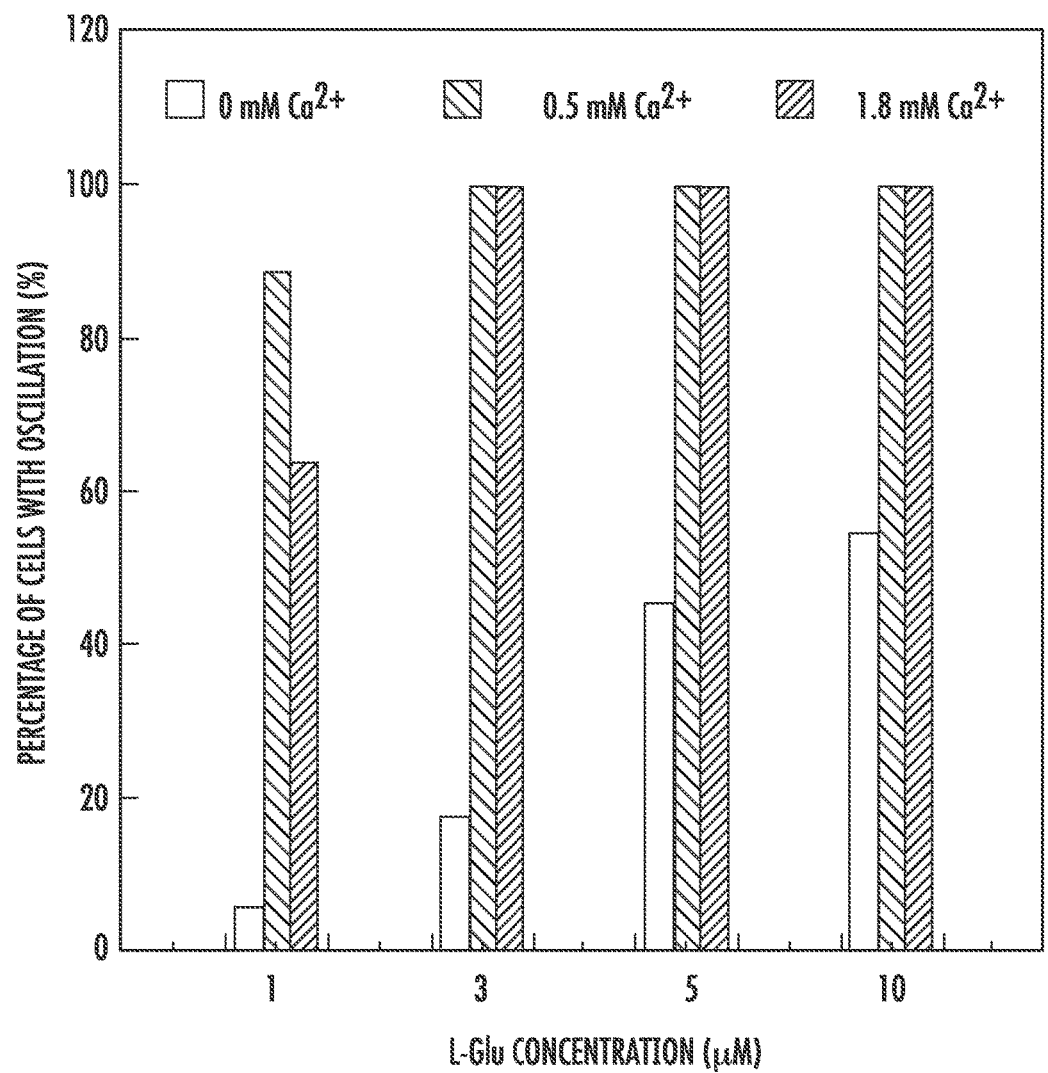
FIG. 12 is a bar graph showing the percentage of cells with oscillation as a response to L-Glu in the presence of different extracellular $Ca^{2+}$. Without extracellular $Ca^{2+}$, low concentration of L-Glu can only trigger very few cells to oscillate (less than 10%), while more than 50% of cells start to oscillate if 0.5 or 1.8 mM is present.
Figure 13A:
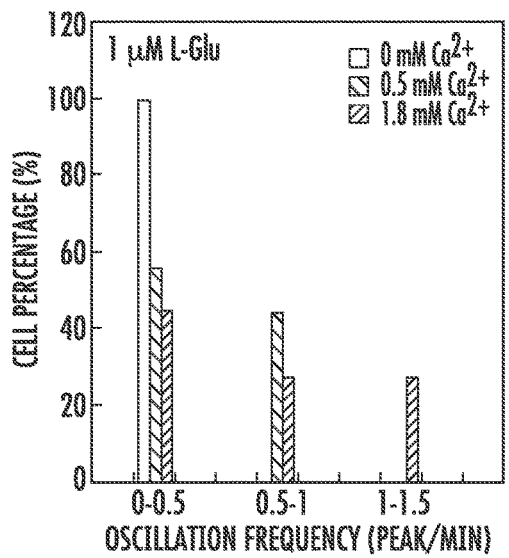
FIG. 13A to 13D are bar graphs showing intracellular $Ca^{2+}$ oscillation frequency of cells incubated with bath solution containing 0, 0.5, or 1.8 mM $Ca^{2+}$ and 1 μM (FIG. 13A), 3 μM (FIG. 13B), 5 μM (FIG. 13C), or 10 μM (FIG. 13D) L-Glu, which was added to activate mGluR5. When the same concentration of L-Glu was applied, more cells incubated in bath solution with higher $Ca^{2+}$ could oscillate at higher frequency.
Figure 13B:
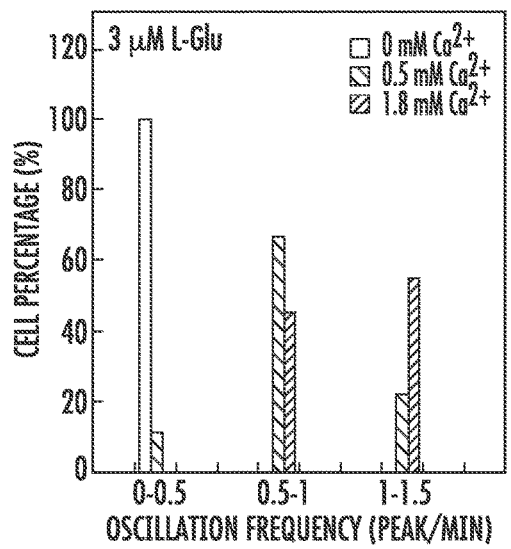
Figure 13C:
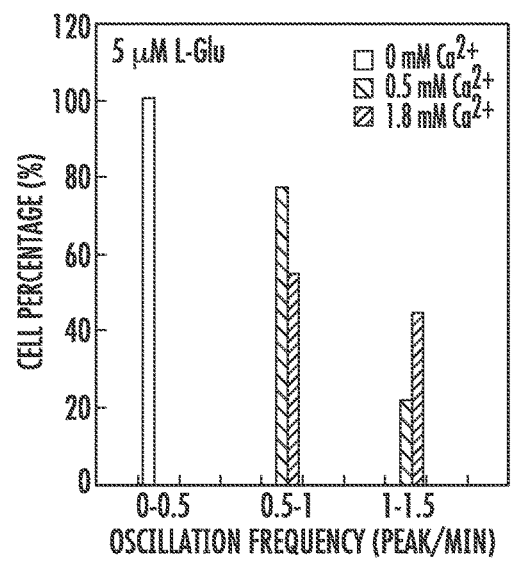
Figure 13D:
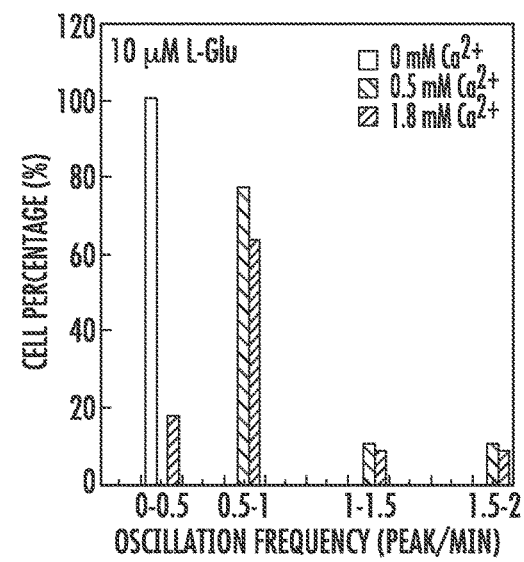

Belong to the group I metabotropic glutamate receptor family, mGluR5 also processes the conserved $Ca^{2+}$ binding site in the extracellular domain. Extracellular $Ca^{2+}$ concentration change induced the intracellular $Ca^{2+}$ oscillation of cells transfected with mGluR5. 0.05 mM extracellular $Ca^{2+}$ concentration change started to induce intracellular oscillation (FIG. 8). Larger extracellular $Ca^{2+}$ concentration changes leaded to higher oscillation frequency (FIGS. 9 and 10).

Example 3

Effects of Extracellular $Ca^{2+}$ on the Response of mGluR5 to L-Glu, Ro-674853 and L-Quis Methods HEK293 cells were cultured and transfected as described above. Intracellular $Ca^{2+}$ concentration was recorded using the method as described previously. In the presence of different extracellular $Ca^{2+}$, L-Glu or Ro-674853 or L-Quis were progressively added to activate mGluR5 and intracellular $Ca^{2+}$ response was monitored.

Results

Extracellular $Ca^{2+}$ Modulating mGluR5 Response to Addition of L-Glu

Cells placed in bath solutions with different concentrations of $Ca^{2+}$ displayed various response to the addition of same amount of L-Glu. In the absence of extracellular $Ca^{2+}$, less percentages of cell could be activated by L-Glu and high L-Glu was needed to potentiate the mGluR. Compared with 0 mM $Ca^{2+}$ bath solution, 1.8 mM resulted in the most percentages of cells to oscillate at low L-Glu (1 M), followed by 0.5 mM $Ca^{2+}$. Besides, intracellular $Ca^{2+}$ oscillation triggered by high concentration of L-Glu in the absence of extracellular $Ca^{2+}$ exhibited much slower oscillation. Extracellular $Ca^{2+}$ can enhance the L-Glu initiated mGluR5 response.

Figure 14A:
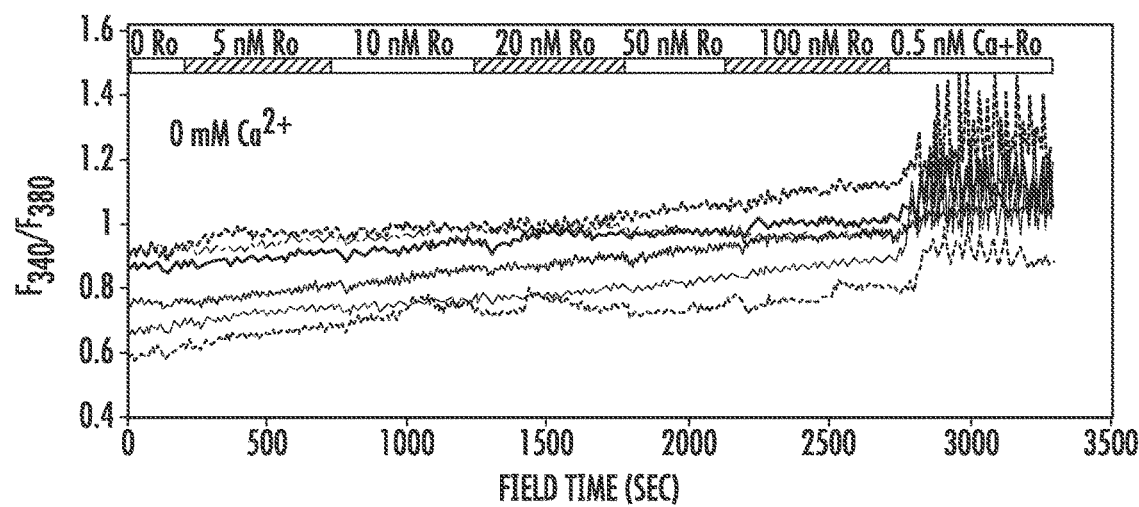
FIG. 14A to 14B shows stimulation of mGluR5 by Ro-674853 in the absence or presence of extracellular $Ca^{2+}$. When no $Ca^{2+}$ was applied in the bath solution (FIG. 14A), Ro-674853 (from 5 to 100 nM) could not stimulate mGluR5, while in the presence of 0.5 mM $Ca^{2+}$ (FIG. 14B), 5 nM Ro-674853 caused high frequency $Ca^{2+}$ oscillation, which suggested mGluR5 was activated.
Figure 14B:
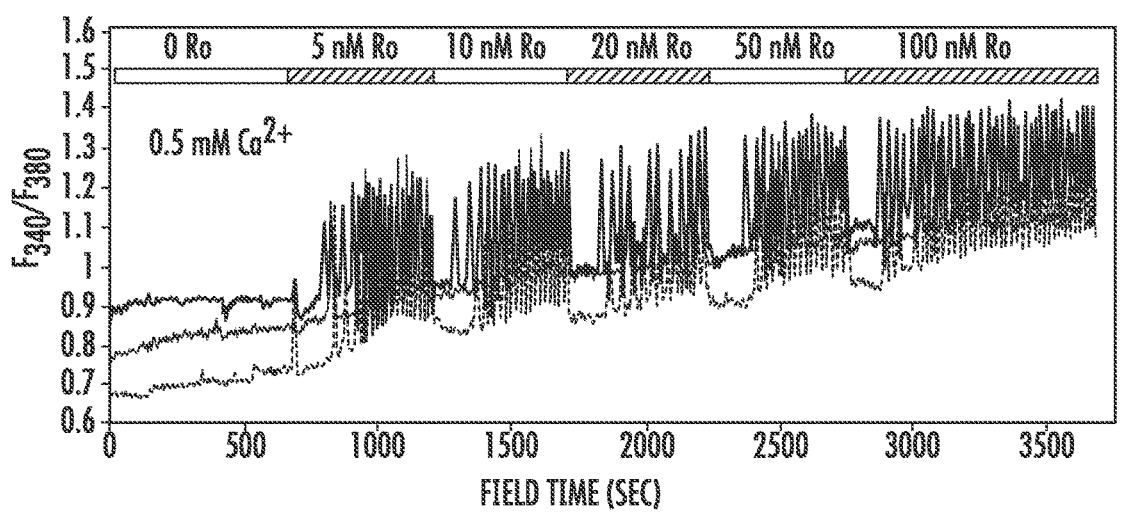

Extracellular $Ca^{2+}$ Modulating mGluR5 Response to Addition of Ro-674853 mGluR5 transfected HEK293 cells were placed in bath solution containing 0 or 0.5 mM $Ca^{2+}$ and Ro-674853 was added to stimulate mGluR5 expressed on the cytoplasmic membrane. In absence of extracellular $Ca^{2+}$, no intracellular $Ca^{2+}$ response was observed, while adding 0.5 mM $Ca^{2+}$ plus Ro-674853 at the end of the experiment can activate the mGluR5 and trigger the intracellular $Ca^{2+}$ oscillation, which indicated that mGluR5 were expressed on the membrane and could be activated. In the presence of 0.5 mM $Ca^{2+}$, high frequency $Ca^{2+}$ oscillation was observed upon the addition of Ro-674853 and 5 nM Ro-674853 could lead to the stimulation of mGluR5 (FIG. 14A to 14B).

Figure 15A:
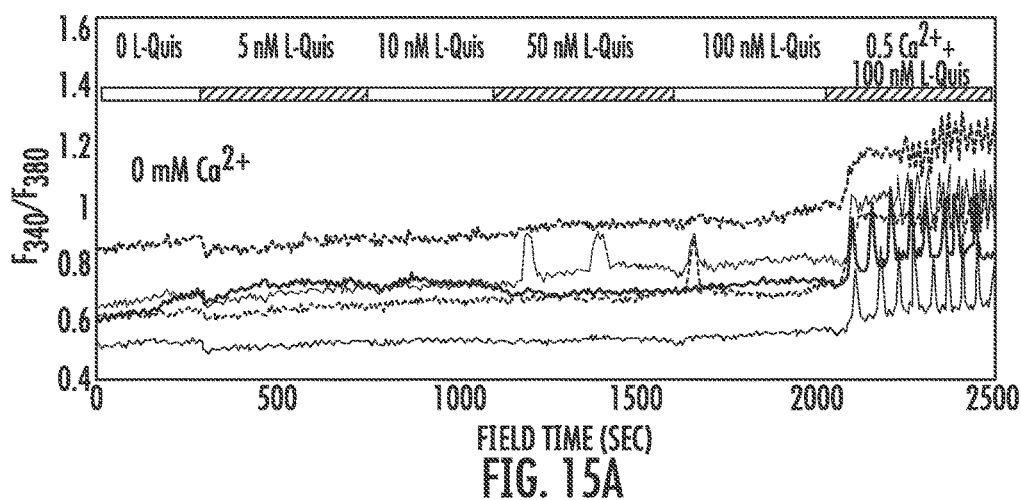
FIG. 15A to 15C show extracellular $Ca^{2+}$ effect on mGluR5 response initiated by L-Quis. Cells presented in the 0 mM $Ca^{2+}$ bath solution hardly showed any response to L-Quis (FIG. 15A), while cells placed in the 0.5 (FIG. 15B) or 1.8 mM (FIG. 15C) $Ca^{2+}$ bath solution exhibited immediate and strong response to the addition of L-Quis. The higher the extracellular $Ca^{2+}$ concentration is, the higher oscillation frequency.
Figure 15B:
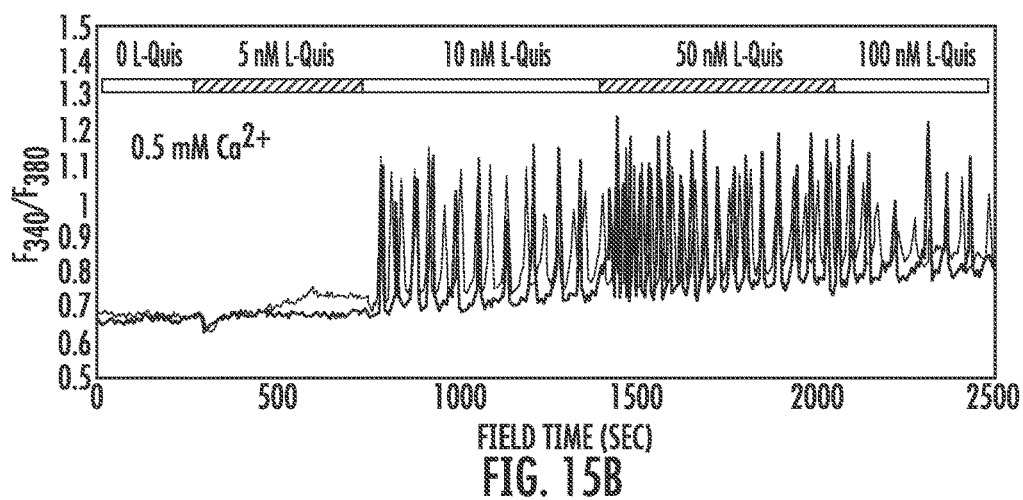
Figure 15C:
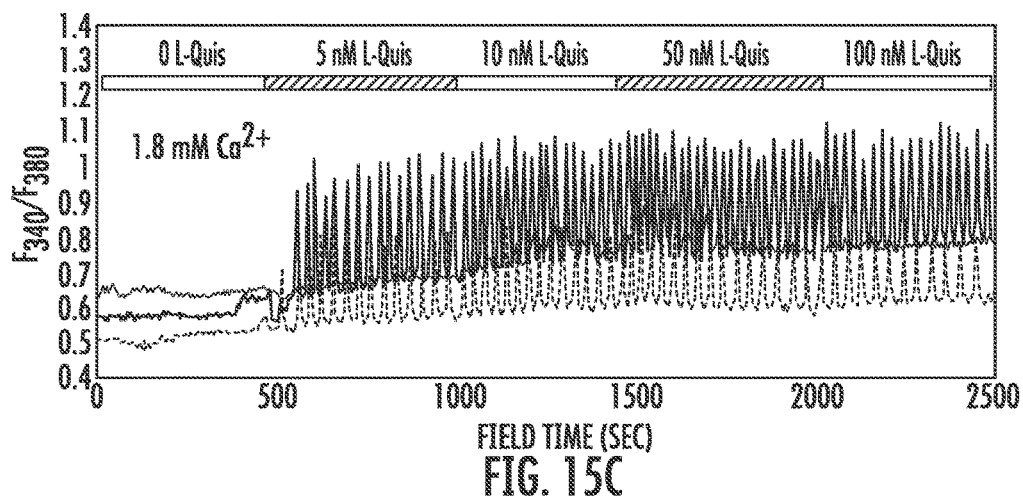
Figure 16A:
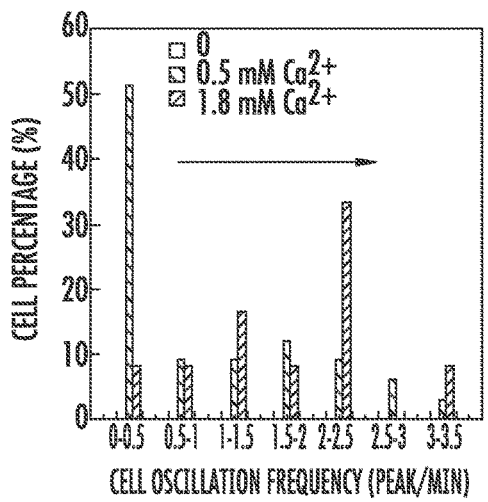
FIG. 16A shows same concentration of L-Quis triggered faster intracellular $Ca^{2+}$ oscillation when placed cells in higher extracellular $Ca^{2+}$ bath solution.
Figure 16B:
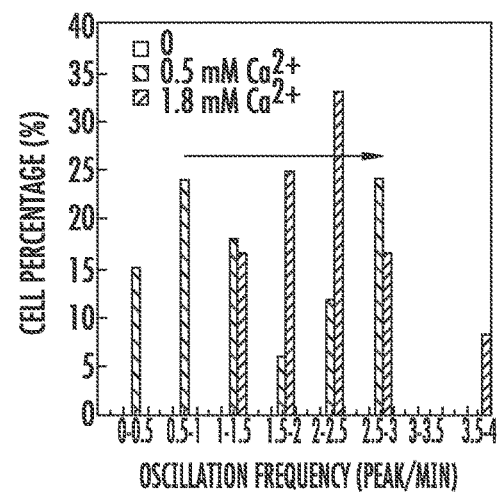
FIG. 16B shows the cell oscillation frequency shifted from left (lower oscillation frequency) to the right (higher oscillation frequency). The arrow in the figure pointed out the shift direction.
Figure 17:
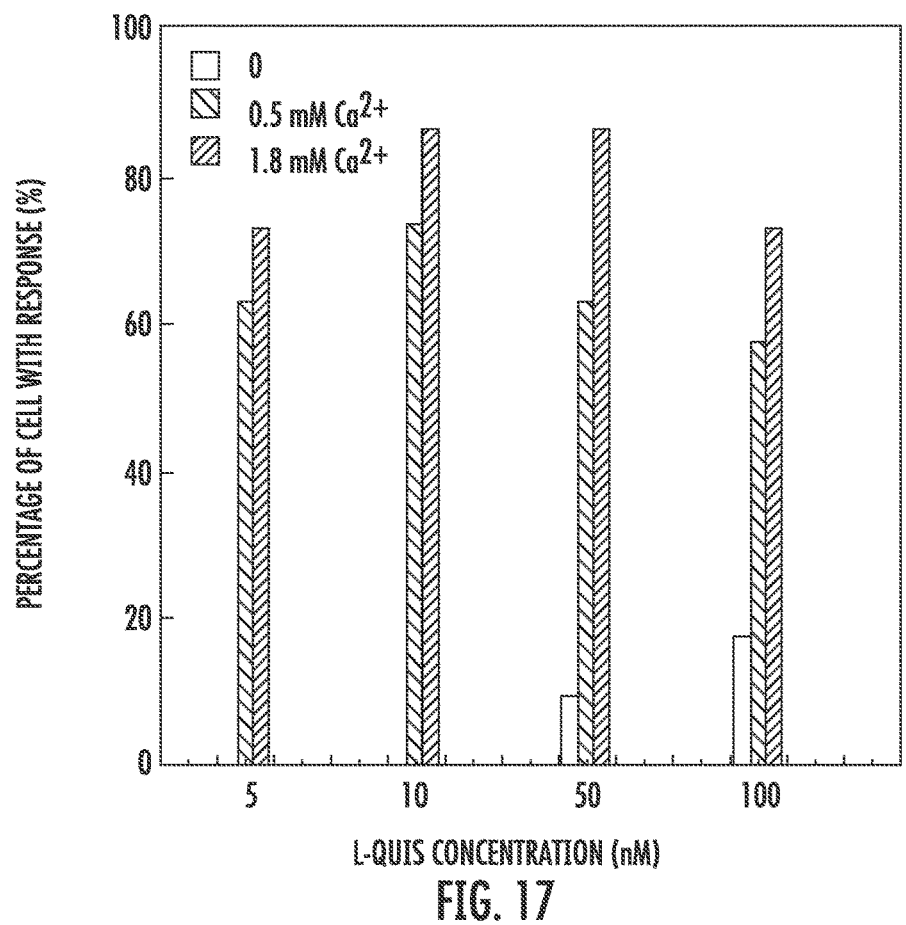
FIG. 17 is a bar graph showing percentage of cells with L-Quis-triggered response. In the absence of extracellular $Ca^{2+}$ addition, higher L-Quis concentration was required to initiate cellular response (less than 20%), while with the addition of extracellular $Ca^{2+}$, 5 nM L-Quis already triggered more than 60% cells to show intracellular $Ca^{2+}$ change.

Extracellular $Ca^{2+}$ Modulating mGluR5 Response to Addition of L-Quis mGluR5 transfected HEK293 cells were placed in bath solution containing 0 or 0.5 mM $Ca^{2+}$ and L-Quis was added to stimulate mGluR5 expressed on the cytoplasmic membrane. Without extracellular $Ca^{2+}$ supply, L-Quis almost could not initiate any mGluR5 response, while cells in the 0.5 or 1.8 mM $Ca^{2+}$ bath solution can be stimulated by addition L-Quis. It is notable that cells in higher $Ca^{2+}$ bath solution started to oscillate at lower L-Quis concentration. Besides, the oscillation frequency is much higher when cells were present in higher $Ca^{2+}$ bath solution (FIGS. 15 and 16). Further analysis indicated that more percentage of cells showed response to the L-Quis stimulation when 0.5 mM or 1.8 mM was applied (FIG. 17).

Example 4 mGluR1 Data Summary

Methods mGluR1-transfected HEK293 cells were grown on 13.5× 20 mm coverslips. After the cells reached 90% confluence, they were loaded by incubation with 4 μM Fura-2 AM in 20 mM HEPES, containing 125 mM NaCl, 5 mM KCl, 1.25 mM CaCl2, 1 mM MgCl2, 1 mM NaH2PO4, 1% glucose, and 1% BSA (pH 7.4) for 1 h at 37° C. and then washed once with 20 mM HEPES, pH 7.4, containing 125 mM NaCl, 5 mM KCl, 0.5 mM CaCl2, 0.5 mM MgCl2, 1% glucose, and 1% BSA (bath buffer). The coverslips with transfected, Fura-2-loaded HEK293 cells were placed diagonally in 3-ml quartz cuvettes containing bath buffer. The fluorescence spectra at 510 nm were measured during stepwise increases in [Ca2+]o with alternating excitation at 340 or 380 nm. The ratio of the intensities of the emitted light at 510 nm when excited at 340 or 380 nm was used to monitor changes in [Ca2+]i. mCherry was genetically fused into mGluR1 pcDNA. so cells have fluorescent intensity at 550 nm was selected for further analysis.

Figure 18:
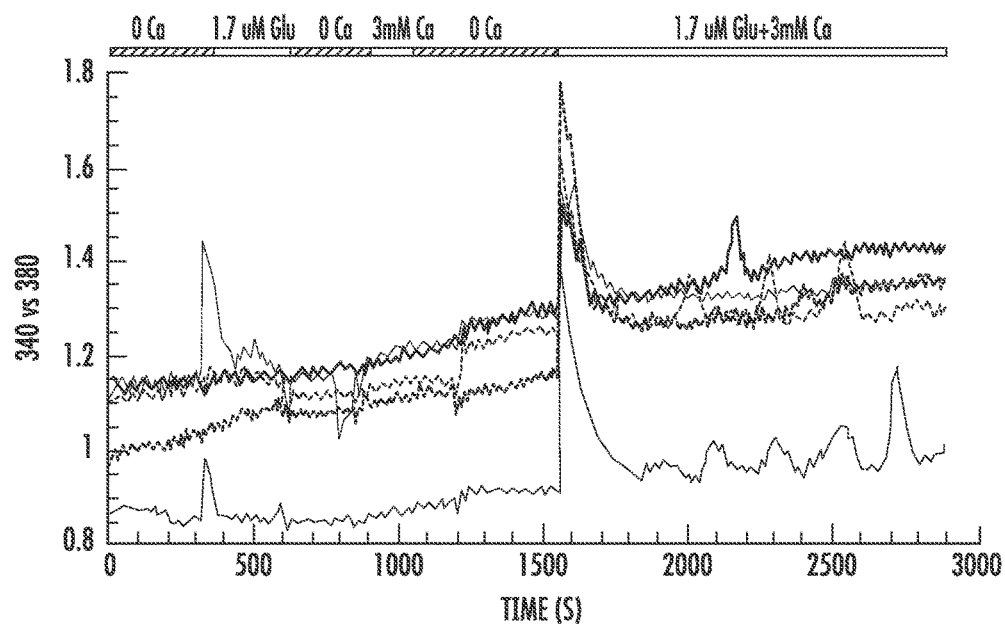
FIG. 18 shows extracellular calcium can enhance glutamate induced intracellular calcium release in mGluR1 transfected HEK293 cells. Ringer buffer with 1.7 uM glutamate/3 mM calcium/1.7 uM glutamate and 3 mM calcium was used to treat cells to study mGluR1 function.
Figure 19:
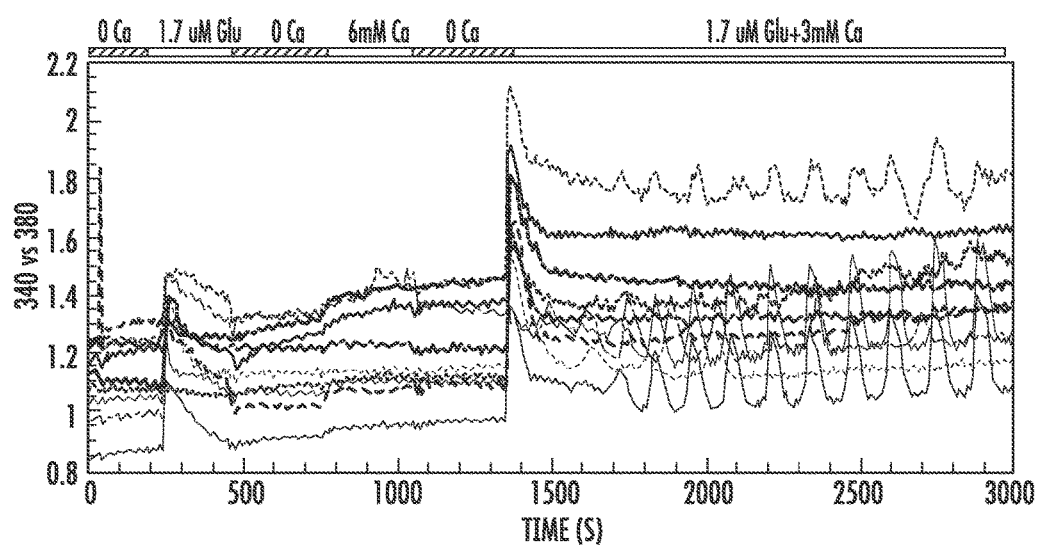
FIG. 19 shows extracellular calcium can enhance glutamate induced intracellular calcium release in mGluR1 transfected HEK293 cells. Ringer buffer with 17 uM glutamate/6 mM calcium/17 uM glutamate and 6 mM calcium was used to treat cells to study mGluR1 function.
Figure 20:
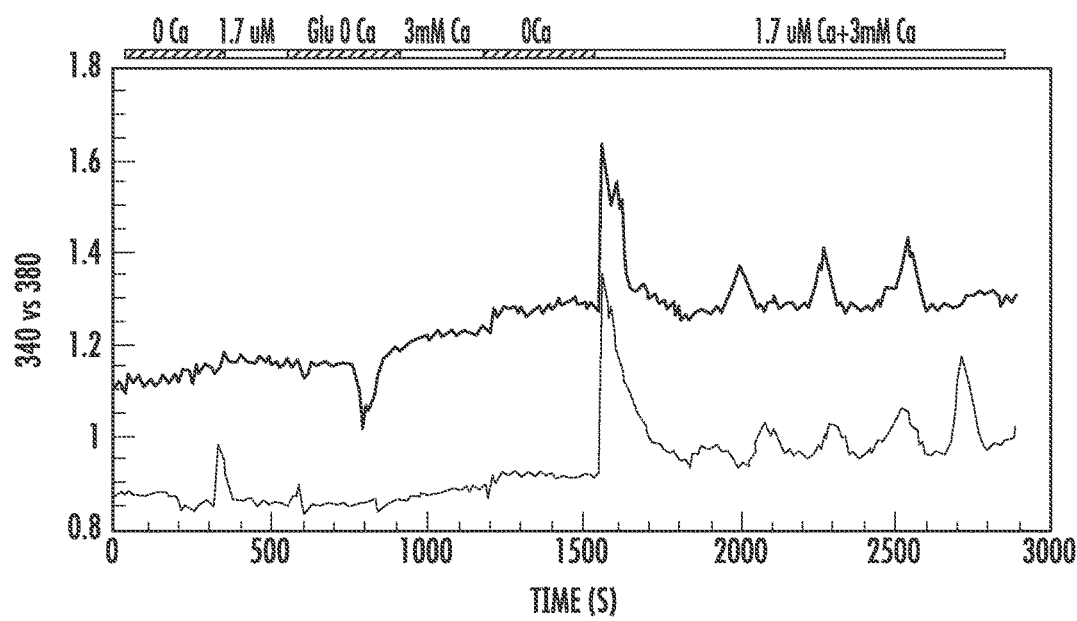
FIG. 20 shows 1.7 uM glutamate and 3 mM extracellular calcium together can trigger intracellular calcium oscillation.
Figure 21:
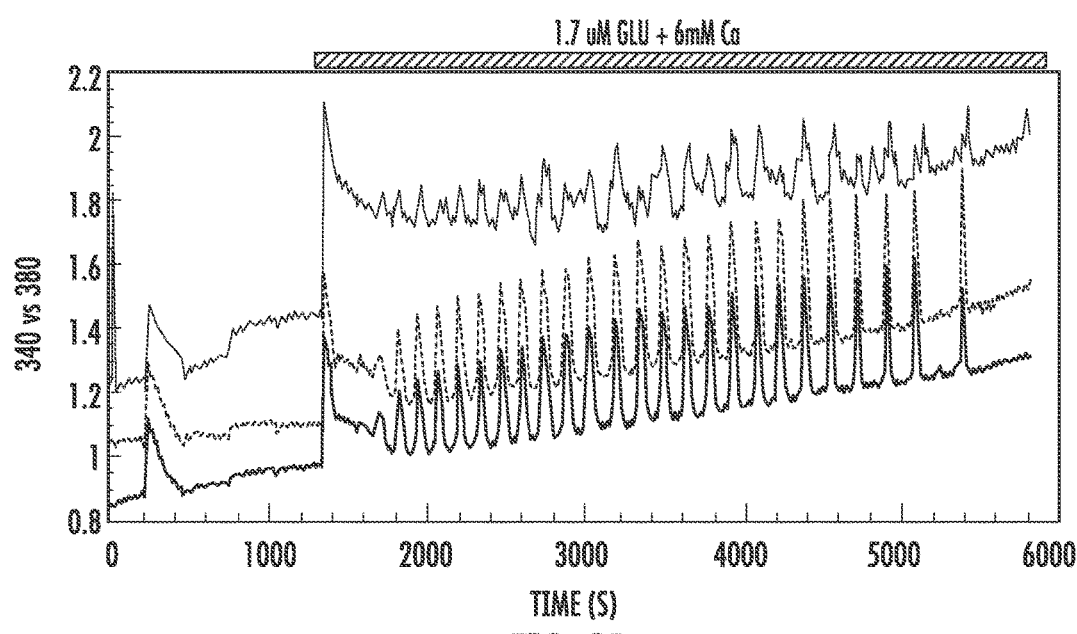
FIG. 21 shows 17 uM glutamate and 6 mM extracellular calcium together trigger intracellular calcium oscillation.

Results mGluR1 can not only be activated by glutamate but also by calcium. Extracellular calcium can enhance glutamate induced intracellular calcium release in mGluR1 transfected HEK293 cell (FIGS. 18 and 19). Glutamate and extracellular calcium together will induce intracellular calcium oscillation (FIG. 20 and FIG. 21). 0 mM calcium was first used to incubate mGluR1 transfected HEK293 cells. The cells were treated by different concentration of glutamate (1.7 uM/17 uM), causing corresponding transient peaks. After peaks return to baseline, 0 mM calcium was further applied to wash away the remaining buffer. And then 3 mM/6 mM calcium were used to trigger the activation of mGluR1, no response was observed. Again, 0 mM calcium was used to wash away the reaming buffer, and finally the cells were treated by glutamate and calcium (1.7 uM glutamate with 3 mM calcium, 17 uM with 6 mM calcium). More cells response and more intracellular calcium was released, meanwhile calcium oscillation was observed (FIGS. 20 and 21). As shown in FIG. 21, calcium oscillation which triggered by Ringer buffer with 17 uM glutamate and 6 mM calcium can last for 1 h. Calcium oscillation frequency is faster and peak amplitude is larger by higher concentration of glutamate and extracellular calcium.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating drug or alcohol addiction that is fully or partially mediated by a group I metabotropic glutamate receptor (mGluR) in a subject comprising:
   administering to the subject:
   (a) a therapeutically effective amount of a negative allosteric modulator of one or more group I mGluRs, and
   (b) a calcium agent for increasing or decreasing extracellular $Ca^{2+}$ levels in an amount to modulate the activity of the negative allosteric modulator,
   wherein the calcium agent is a food or calcium supplement which is administered in an amount sufficient to reach an elemental calcium amount from about 100 mg to about 5000 mg.

2. The method of claim 1, wherein the one or more group I mGluRs are selected from the group consisting of mGluR1 and mGluR5.

3. The method of claim 1, wherein the negative allosteric modulator is selected from the following molecules: [3H]R214127; NPS2390; R214127; 9-dimethylamino-3-(4-ethylphenyl)-3H-5-thia-1,3,6-triazafluoren-4-one; CPCCOEt; A841720; 3,5-dimethyl PPP; DM-PPP; YM298198; BAY 367620; EM-TBPC; LY456236; [3H]fenobam; BOMA; MTEP; MTEB; [3H]M-MPEP; [14C]MTEP; MPEP; fenobam; PTeB; SIB-1757; and SIB-1893.

4. The method of claim 1, wherein the negative allosteric modulator is formulated with the calcium agent in a single dosage unit.

5. The method of claim 1, wherein the negative allosteric modulator comprises CPCCOEt.

* * * * *

```
                         SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Gly Gly Asn Ser Gly Gly
1               5
```